United States Patent [19]

Ramachandran

[11] Patent Number: 5,691,799
[45] Date of Patent: Nov. 25, 1997

[54] METHOD AND APPARATUS FOR MEASURING VERTICAL AND HORIZONTAL PUPILLARY DECENTRATION

[76] Inventor: Narayanan Ramachandran, 5G Fernwood Dr., Bolingbrook, Ill. 60440

[21] Appl. No.: 700,987

[22] Filed: Aug. 21, 1996

Related U.S. Application Data

[63] Continuation-in-part of Ser. No. 595,024, Jan. 31, 1996, Pat. No. 5,640,219.
[51] Int. Cl.$^6$ .................. A61B 3/10; A61B 3/00
[52] U.S. Cl. .................. 351/204; 351/246; 33/200
[58] Field of Search .................. 351/200, 204, 351/205, 245; 33/200

[56] References Cited

U.S. PATENT DOCUMENTS

| | | | |
|---|---|---|---|
| 2,491,312 | 12/1949 | Henry et al. | 33/200 |
| 3,495,897 | 2/1970 | Deforges | 351/204 |
| 3,981,081 | 9/1976 | Welch | 33/174 A |
| 3,987,554 | 10/1976 | Pastore | 33/200 |
| 4,055,900 | 11/1977 | Grolman et al. | 33/200 |
| 4,208,800 | 6/1980 | Grolman et al. | 33/200 |
| 4,653,192 | 3/1987 | Conrad et al. | 33/200 |
| 4,653,881 | 3/1987 | Joncour | 351/204 |
| 5,167,074 | 12/1992 | Weiss | 33/200 |
| 5,379,079 | 1/1995 | Kratky | 351/204 |

Primary Examiner—Huy Mai
Attorney, Agent, or Firm—Welsh & Katz, Ltd.

[57] ABSTRACT

The present invention measures the vertical and horizontal decentration of a pupil of a patient relative to a spectacle frame. The apparatus includes a housing having a distal end defining at least one target aperture. The housing has a proximal end opposite the distal end. An eye-piece is disposed at the proximal end and permits an operator to observe the pupil of the patient through the target aperture such that the eye-piece, the target aperture, the spectacle frame, and the pupil of the patient are in operative alignment. Also included is an adjustable left, right, and center vertical reference marker, each operatively coupled to the housing and horizontally displaceable relative thereto. The left and right vertical reference markers are configured to determine the position of a temporal edge and a nasal edge of the spectacle frame, respectively, while the center vertical reference marker is configured to be vertically aligned with the center of the pupil. The left, right, and center vertical reference markers are operatively coupled to a circuit which provides an electrical signal corresponding to a measurement of a horizontal distance between the center vertical reference marker and the left and right reference markers, respectively. This horizontal distance represents horizontal decentration.

14 Claims, 10 Drawing Sheets

METHOD AND APPARATUS FOR MEASURING VERTICAL AND HORIZONTAL PUPILLARY DECENTRATION

This patent application is a Continuation-in-Part of Ser. No. 08/595,024 entitled Apparatus for Measuring Pupillary Height, filed Jan. 31, 1996 and now U.S. Pat. No. 5,640,219.

BACKGROUND OF THE INVENTION

The present invention relates generally to an apparatus for measuring parameters required for mounting ophthalmic lenses in a spectacle frame and more specifically to obtaining horizontal decentration while measuring horizontal pupillary distance in combination with obtaining the raise or drop (vertical decentration), while measuring the pupillary height. The measurements are obtained by considering the position of the pupil of the eye with respect to the top and bottom edges of the spectacle frame, and with respect to the nasal and temporal edges of the spectacle frame.

In order to determine the pupillary height for placement of progressive addition lenses, a standard rule or scale has been typically used to estimate the height of the center of the pupil with respect to the lowest part of the lower eye wire of the spectacle frame so that the measurements can be conveyed to the lens maker. However, in such manual ruler techniques, inaccuracy can be easily introduced, resulting in patient dissatisfaction.

An example of such a known ruler-type gauge is disclosed in U.S. Pat. No. 3,987,554 issued on Oct. 26, 1976 to J. Pastore. The known gauge is inserted into the bevel (lens well) of the lower eye wire of the spectacle frame at its lowest part, and by reading the graduation where an imaginary horizontal line passing through the center of the pupil would intersect the gauge, the pupillary height is estimated. However, the device is inconvenient to use and is prone to measurement errors caused by the following factors: 1) the patient's eyes may wander; 2) the optician approximates the center of the corneas or pupil by observation; 3) the optician approximates the imaginary line; 4) the optician approximates the lowest portion of the lower eye wire; and 5) proximity between the patient and the optician could cause eye strain to both the patient and the optician.

Other devices exist which include an ocular or eye-piece through which the optician observes the eye of the patient. The eye-piece typically includes a cross-hair or horizontal line which is aligned with the center of the eye. An example of such a known ocular positioning apparatus is disclosed in U.S. Pat. No. 5,167,074 issued on Dec. 1, 1992 to M. Weiss. The device provides a chin rest for maintaining the stability of the patient's head. The optician observes the center of the eye or other reference points on the patient's face through an ocular and moves the ocular along a vertical axis until the cross-hairs of the ocular are aligned with the appropriate reference point. The vertical distance traveled by the ocular represents the pupillary height of the patient.

However, such a known device is extremely cumbersome and requires placement on a suitable table top and is preferably, permanently mounted to the table top. A significant drawback of this device is that the cross-hairs of the optician's eye-piece are disposed relatively far away from the patient's eye. When the optician attempts to align the cross-hairs with the eye, the measurement of the distance, or the vertical distance that the eye-piece is displaced, depends upon the angle through which the optician views the patient's eye. This may result in a significant parallax error. During each attempt to align the cross-hairs with the eye, the optician must look through the exact center of the eye-piece to avoid introduction of such parallax errors. This task is difficult to accurately perform and often results in measurement errors.

Additionally, a measurement of decentration, or a horizontal measurement of the position of the pupil with respect to the center of the spectacle frame (or more specifically, with respect to the center of the "A" measurement of the spectacle frame) is desirable. In certain cases, a measurement of "raise" or "drop" or vertical measurement of the position of the pupil with respect to the center of the "B" measurement of the spectacle frame is also desirable.

Typically the optician performs the following steps:

1. The pupillary half spacing or one-half the distance between the pupil centers of the patient is measured using a known device.

2. The distance between the center of the frame that the patient has selected is measured using a rule. This measurement is also equal to the "A" measurement of the spectacle frame plus the DBL measurement (distance between the lenses).

3. The decentration is manually calculated by subtracting the pupillary half spacing from one-half of the distance between the spectacle frame centers.

4. Similarly, the optician again measures the pupillary height of the patient wearing the selected frame.

5. The "B" measurement of the frame is measured.

6. The vertical decentration, referred to as "raise/drop", is calculated by subtracting one-half of the "B" measurement from the pupillary height measured. If the result is a positive number, it is defined as a raise. If it is a negative number, it is defined as a drop.

Known devices typically measure one-half of the distance between the pupil centers. This distance is referred to as the "monocular PD". Such a device is disclosed in U.S. Pat. No. 4,653,881 issued on Mar. 31, 1987 to Joncour. However, the device is not configured to measure either the horizontal or the vertical decentration.

Usually, the optician desires to obtain measurements for both vertical and horizontal decentration, and must perform the laborious steps described above. Presently, the optician must use at least two separate devices to obtain both measurements, where each device has the above-described deficiencies. This procedure is inefficient and time consuming.

Accordingly, it is an object of the present invention to substantially overcome the above-described problems.

It is another object of the present invention to provide a novel device to measure vertical and horizontal decentration where parallax error is substantially eliminated.

It is a further object of the present invention to provide a novel device to measure horizontal decentration from the position of the center of the pupil with respect to the nasal and temporal edges of the spectacle frame, and to measure the vertical decentration from the position of the center of the pupil with respect to the top and bottom edges of the spectacle frame.

It is another object of the present invention to provide a novel device to measure horizontal and vertical decentration with a single device, where such measurements are obtained during a single sitting of the patient.

It is also an object of the present invention to provide a novel device to measure horizontal and vertical decentration which independently measures the horizontal and vertical decentration of each eye.

It is still an object of the present invention to provide a novel device to measure horizontal and vertical decentration that is very accurate, is physically compact, and is easy to operate.

SUMMARY OF THE INVENTION

The disadvantages of known procedures for finding the horizontal and vertical decentration are substantially overcome with the present invention by providing a novel device for accurately measuring the horizontal decentration from the position of the center of the pupil with respect to the nasal and temporal edges of the spectacle frame, and for measuring the vertical decentration from the position of the center of the pupil with respect to the top and bottom edges of the spectacle frame. The apparatus is compact and is easy to use such that technicians can be easily trained to use the device and obtain accurate readings.

The optician need only sit the patient on a height adjustable stool and have the patient rest his or her chin on the chin rest and his or her forehead against a centrally disposed adjustable forehead rest. The optician then adjusts the forehead rest so that the patient's line of sight is directed into the apertures of the apparatus.

To obtain vertical decentration, the optician adjusts top and bottom horizontal platforms so that the platforms contact his or her top and bottom edges of the spectacle frame respectively. Once the platforms are adjusted, the optician observes the patient's eyes through the eye-piece and aligns a horizontal reference marker with the corneal reflection. The intersection of the horizontal reference marker, as seen through the eye-piece, relative to the platforms, directly corresponds to the measurement of vertical decentration or vertical distance relative to the top and bottom edges of the spectacle frame. Due to the fact that the corneal reflection, the horizontal reference marker, and the ocular are all at the same height as the optician looks through the ocular, virtually no parallax error occurs.

Similarly, horizontal decentration is measured. To measure horizontal decentration, three vertical reference markers are used for measuring each eye. For the right eye of the patient, the left and right vertical reference markers are aligned with the temporal and nasal edges of the spectacle frame, respectively. A center vertical reference marker is then aligned with the corneal reflection of the patient's eye, and the decentration measurement is recorded. The same procedure is performed with respect to the left eye.

More specifically, the method and apparatus for measuring horizontal and vertical decentration of the present invention permits measurement of the horizontal and vertical decentration of a pupil of a patient relative to a spectacle frame that the patient has selected.

The apparatus includes a housing having a distal end defining at least one target aperture. The housing has a proximal end opposite the distal end. An eye-piece is disposed at the proximal end and permits an operator to observe the pupil of the patient through the target aperture such that the eye-piece, the target aperture, the spectacle frame, and the pupil of the patient are in operative alignment.

Also included is an adjustable upper, lower, and center horizontal reference marker, each operatively coupled to the housing and vertically displaceable relative thereto. The upper and lower horizontal reference markers are configured to determine the position of an upper edge and lower edge of the spectacle frame, respectively, while the center horizontal reference marker is configured to be aligned with and intersect a center of the pupil.

The upper, lower, and center horizontal reference markers are operatively coupled to a circuit which provides an electrical signal corresponding to a measurement of a vertical distance from the center of the separation between the upper and lower reference markers to the position of the central horizontal reference marker. In addition to the vertical distance, an electrical signal also provides the direction of displacement of the central reference marker from the center of the separation between the upper and lower reference markers. This vertical distance, along with the direction, represents vertical decentration.

Also included for each eye is an adjustable left, right, and center vertical reference marker, each operatively coupled to the housing and horizontally displaceable relative thereto. For the right eye of the patient, the left and right vertical reference markers are configured to determine the position of a temporal edge and the nasal edge of the spectacle frame, respectively. The center vertical reference marker is configured to be aligned with and intersect the center of the pupil. The left, right, and center vertical reference markers are operatively coupled to a circuit which provides an electrical signal corresponding to a measurement of a horizontal distance and a direction from the center of the separation between the left and right (temporal and nasal) vertical reference markers to the position of the central vertical reference marker. This horizontal distance and direction of displacement from the center of the pupil to the center of the separation between the nasal and temporal edges of the frame, represents horizontal decentration.

BRIEF DESCRIPTION OF THE DRAWINGS

The features of the present invention which are believed to be novel are set forth with particularity in the appended claims. The invention, together with further objects and advantages thereof, may best be understood by reference to the following description in conjunction with the accompanying drawings.

DETAILED DESCRIPTION OF THE INVENTION

Figure 1:
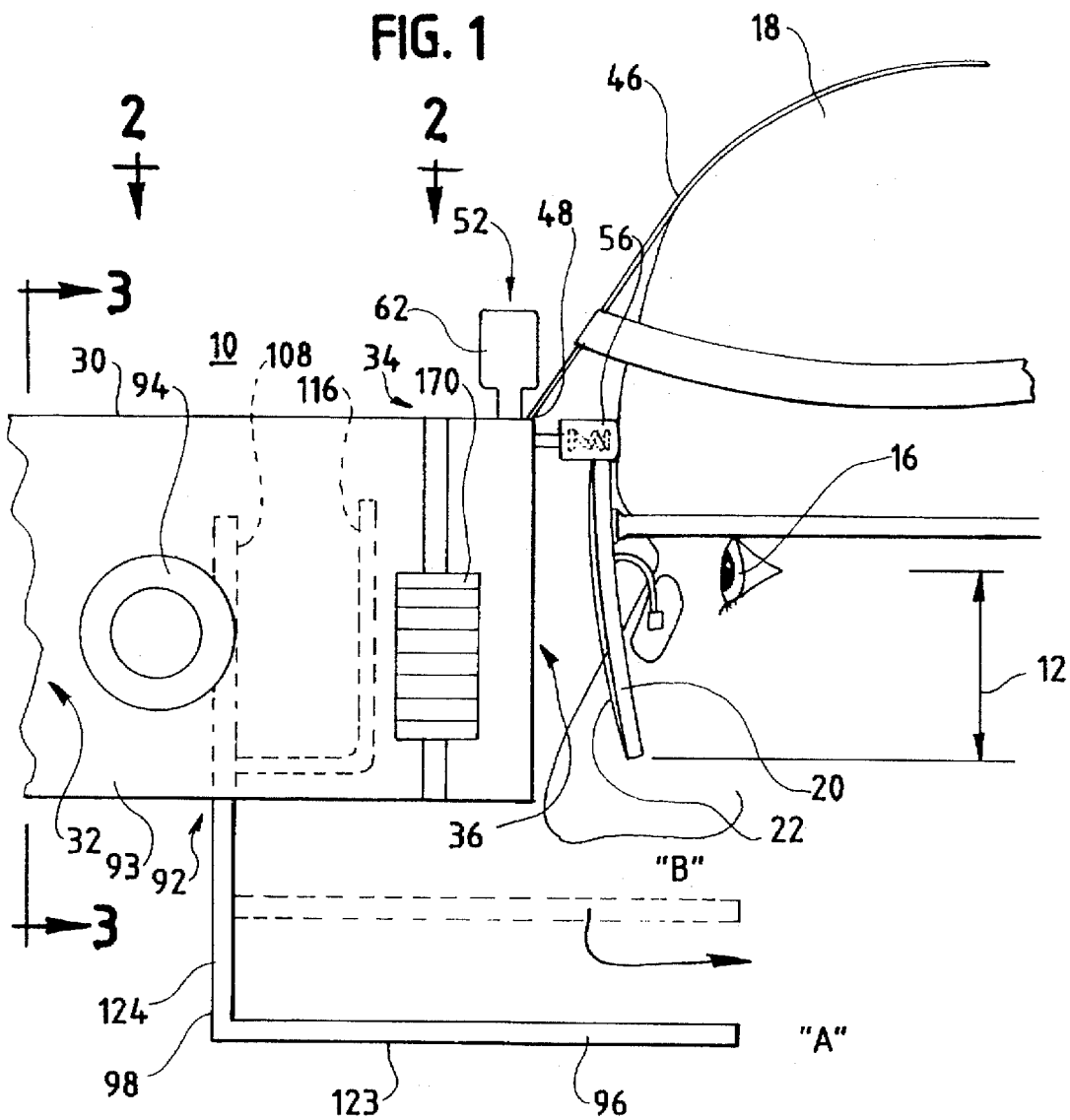
FIG. 1 is a side elevational view of a specific embodiment of a pupillary height measuring apparatus, according to the present invention.
Figure 2:
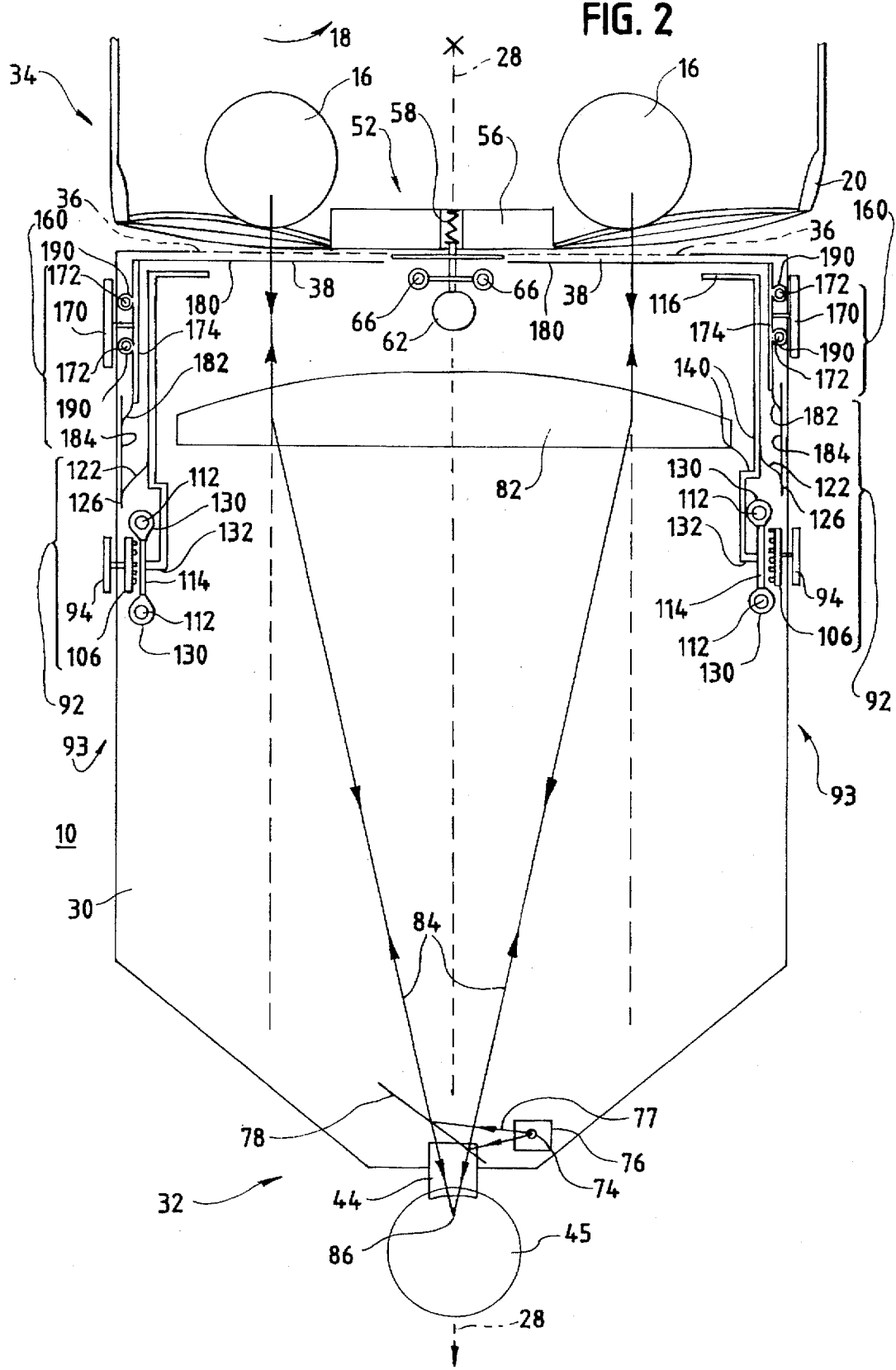
FIG. 2 is a top plan sectional view of the pupillary height measuring apparatus shown in FIG. 1, taken along the line 2—2 of FIG. 1 in the direction generally indicated.
Figure 3:
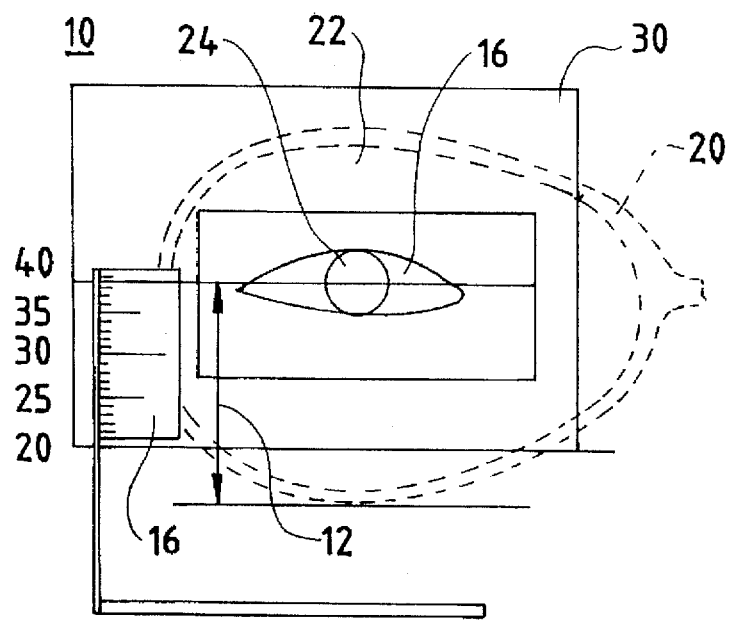
FIG. 3 is a front sectional view of the pupillary height measuring apparatus shown in FIG. 1, taken along the line 3—3 of FIG. 1 in the direction generally indicated, particularly showing the measured height parameters of the eye.

Referring now to FIGS. 1-3, an apparatus 10 for measuring pupillary height is shown generally in FIGS. 1 and 2. FIGS. 1 and 2 illustrate the apparatus 10 while FIG. 3 illustrates the particular height parameter measured. The apparatus 10 measures pupillary height 12 (FIG. 3) of each eye 16 of a patient 18 relative to a spectacle frame 20 where the frame contains a pair of lenses 22. It is extremely important to measure the exact pupillary height 12 when mounting progressive lenses in the frame 20. The pupillary height 12 is the distance between the center of the patient's pupil 24 (as determined by the corneal reflection, described in greater detail hereinafter) and the lowest portion of the lower eye wire of the spectacle frame 20. Alternately, as described hereinafter, the pupillary height 12 may be measured with respect to both the top and bottom edges of the spectacle frame 20.

Note that all lateral components shown in FIG. 2 are symmetric about a longitudinal axis 28 and that the left half of the apparatus 10 is identical to the right half of the apparatus. Accordingly, identical reference numerals identify like structures. A housing 30 is provided which may be constructed from plastic or metal or any other suitable material. As best seen in FIG. 2, the housing 30 is generally rectangular or box-like in shape and may taper toward a proximal end 32, for aesthetic reasons. Alternately, the housing 30 may be rectangular and flat on all sides. A distal end 34, disposed opposite the proximal end 32, is relatively flat and defines two target apertures 36 each having a protective transparent glass or plastic covering 38 (FIG. 2) through which the patient's 18 line of sight is directed. The eyes 16 of the patient 18 are directed such that they are in operative alignment with an eye-piece or ocular 44 disposed at the proximal end 32. An optician or technician 45 observes the patient's eyes 16 through the eye-piece 44 and through the target apertures 36 and performs the required measurements, as will be described in greater detail below.

A flexible band 46 (FIG. 1) is configured to wrap around the forehead of the patient 18 to fixedly secure and maintain the housing 30 relative to the patient. The band 46 may be formed from soft plastic or fabric and may be stretchable to conform to different head sizes, including adults and children. Alternately, the band 46 may be adjustable having belt-like adjustments or may include hook and loop-type fasteners, as is known in the art. The band 46 is pivotally mounted to the distal end 34 of the housing and is configured to pivot vertically relative to the patient 18. The apparatus 10 is preferably centered on the forehead of the patient 18 so as to maintain the longitudinal axis 28 (FIG. 2) in a centered orientation with respect to the patient's eyes 16. Accordingly, as the housing 30 is upwardly pivoted with respect to the band 46, the distal end 34 moves away from the patient's face. Conversely, as the housing 30 is downwardly pivoted with respect to the band 46, the distal end 34 moves closer to the patient's face. A hinge 48 couples the band 46 to the housing 30 to achieve the above-described relationship between the band and the housing. The hinge 48 inhibits lateral movement of the patient 18 with respect to the housing 30 so that the patient is always centered with respect to the longitudinal axis 28 (FIG. 2).

Alternately, the band 46 may be replaced with a soft cushioning footer or rubber bumper (not shown) attached to the housing 30. The footer is gently pressed against the patient's 18 forehead since the apparatus 10 is relatively light in weight permitting the optician 45 to hold the apparatus 10 in place while performing the measurement. The optician 45 preferably holds the apparatus 10 in a steady manner while performing the task.

Figure 4:
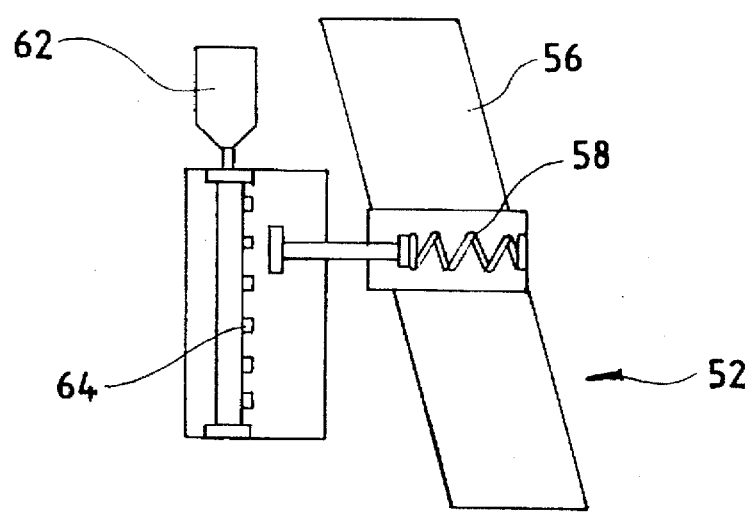
FIG. 4 is an enlarged side view of an upper guide shown in FIG. 2.

Referring now to FIGS. 2 and 4, FIG. 4 illustrates an upper guide mechanism 52 connected to the housing 30. The upper guide mechanism 52 is configured to extend away from the housing 30 to engage a top edge of the spectacle frame 20 to establish and maintain the housing at a fixed vertical height relative to the spectacle frame. The upper guide mechanism 52 includes a planar shelf 56 which extends away from the housing 30. The shelf 56 extends outwardly and is adjusted vertically until it contacts the top edge of the spectacle frame 20. The shelf 56 is biased outwardly toward the patient 18 with a spring 58 so that the shelf contacts the forehead of the patient while simultaneously contacting the top edge of the spectacle frame 20.

The planar shelf 56 is adjusted in the vertical direction by turning an upper guide adjustment knob 62. The knob 62 is connected to a threaded bolt or worm gear 64 (FIG. 4) which is secured within the housing by a sleeve and upright rail arrangement 66 (FIG. 2), as is known in the art. When the knob 62 is rotated in the clockwise direction, the planar shelf 56 moves upwardly. Conversely, when the knob 62 is rotated in the counter-clockwise direction, the planar shelf 56 moves downwardly. Thus, the upper guide mechanism 52 establishes the housing 30 at a fixed vertical height relative to the spectacle frame 20 so that repeatable measurements may be taken. However, any suitable means for fixing the vertical height between the housing 30 and the spectacle frame 20 may be used. Note, that the relative position between the housing 30 and the spectacle frame 20 does not affect the measurement of pupillary height 12 (FIG. 3), as will be described in greater detail hereinafter. The upper guide 56 is configured to prevent the spectacle frame 20 from moving upwards relative to the patient's 18 habitual wearing position when the lower platforms 96 engage the lower eyewires of the frame 20.

Referring now to FIG. 2, the optics of the apparatus 10 are shown generally. A light source 74 is disposed in a shielded housing 76 and directs a beam of light 77 toward a planar mirror 78 disposed at a forty-five degree angle to the incident light beam. The planar mirror 78 reflects the light toward a convex lens 82 along a light path indicated by reference numeral 84. The convex lens 82 is disposed toward the distal end 34 of the housing 30 and refracts the light beam 84 into the patient's eyes 16 in a parallel configuration. The light is then reflected off of the cornea of the eyes 16 and is retraced through the convex lens 82 toward the optician 45. A portion of the reflected light passes just below the planar mirror 78 and enters the ocular 44 and is viewed by the optician 45. In this way, the optician 45 can see the image of the light source 74 as the corneal reflection of the patient's eyes 16. This establishes the exact center of the pupil of the eye 16. The planar mirror 78 may also be partially transmissive so that the optician 45 can view a portion of the light reflected back from the patient 18 as it passes through the mirror 78.

The convex lens 82 is selected so that its focal length allows the light from the light source 74 to be rendered in a parallel orientation toward the patient's eyes 16. Further, the focal length of the lens 82 is the same distance as the distance between the light source 74 and the lens. This distance is also equal to the distance between the lens and the point 86 where the light converges inside the optician's 45 eye.

Figure 5:
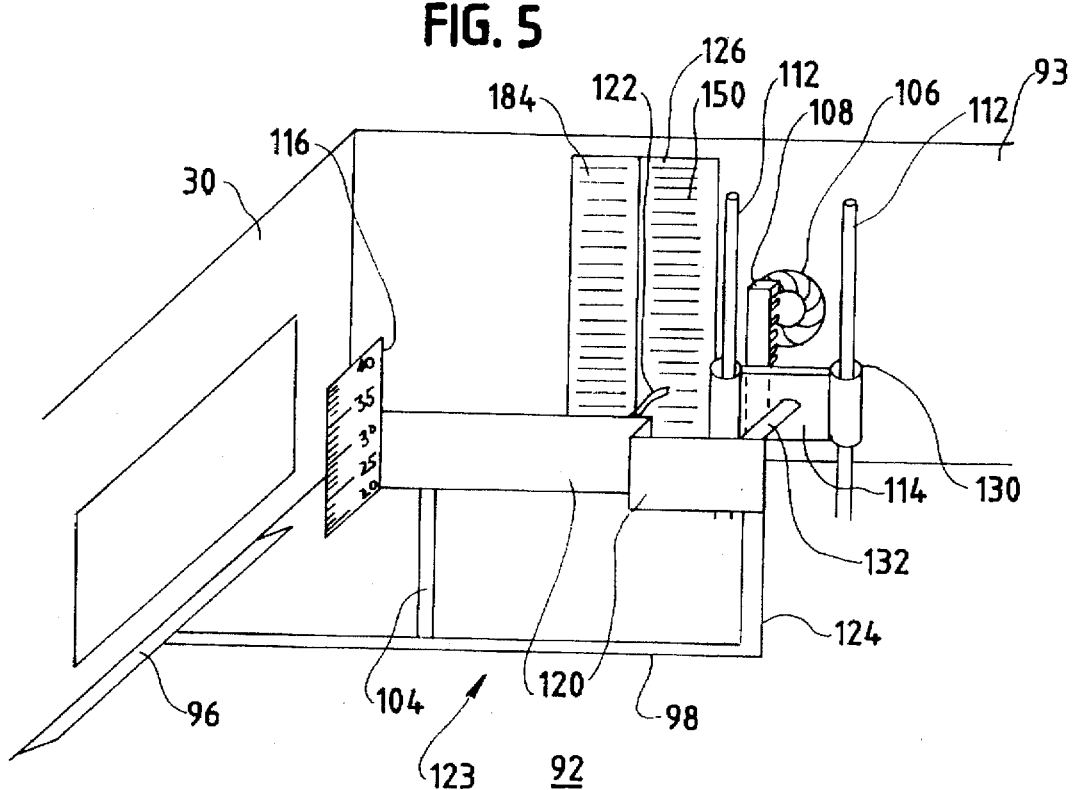
FIG. 5 is an enlarged perspective view of a lower platform mechanism shown in FIG. 2.
Figure 6:
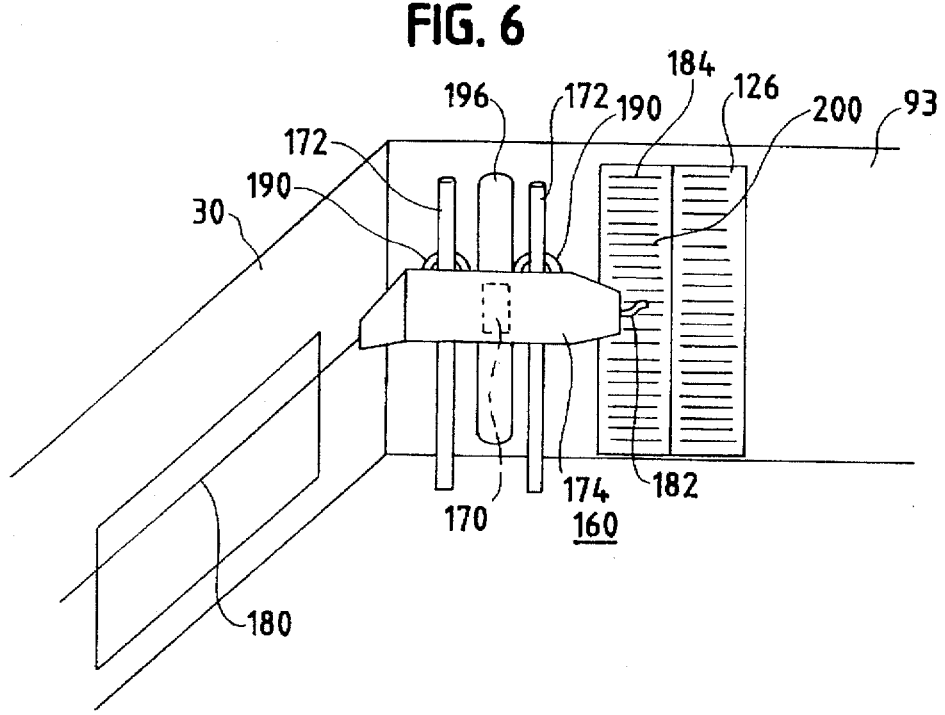
FIG. 6 is an enlarged perspective view of a horizontal reference marker mechanism shown in FIG. 2.

Referring now to FIGS. 1, 2 and 5, FIG. 2 shows the housing 30 and a top view of a lower platform mechanism 92 generally, while FIG. 5 illustrates an enlarged detailed illustration of the right side lower platform mechanism shown from within the housing. Note that two lower platform mechanisms 92 exist, each disposed on opposite lateral sides 93 of the housing 30 and directed toward measuring the pupillary height 12 of the left and right eye, respectively. Each lower platform mechanism 92 is independently adjustable relative to the other to facilitate measurement of the pupillary height 12 of each eye 16 independently.

The lower platform mechanism 92 includes an adjustment knob 94 (FIGS. 1–2), a lower platform 96 (FIG. 1 and 5), a lower platform support arm 98 (FIGS. 1 and 5), a lower platform brace 104, a crown wheel 106, a toothed rod 108, guide rails 112, a lower platform slider body 114, a measuring scale 116, a scale support arm 120, an electrical wiper 122, and a printed circuit board 126. The function of the lower platform mechanism 92 is to move the lower platform 96 in a vertical direction until the lower platform engages the bottom edge of the patient's spectacle frame 20. Accordingly, the lower platform 96 is external to the housing 30 and is supported by the lower platform support arm 98 which extends outside of the housing but enters the housing through an aperture (not shown) in the bottom of the housing. The lower platform brace 104 (FIG. 5) may be included to prevent the lower platform support arm 98 from flexing such that the lower platform 96 is maintained in a parallel orientation relative to the bottom of the housing 30.

The lower platform support arm 98 is formed from a horizontal portion 123 (FIGS. 1 and 5) and a vertical portion 124 connected to the horizontal portion at substantially ninety degrees. The horizontal portion 123 is disposed substantially external to the housing 30 and extends away from the housing 30 to permit the lower platform 96 to be displaced vertically until it contacts the lower edge of the spectacle frame 20. The vertical portion 124, including the lower platform brace 104 (not shown in FIG. 1) is partially received within the housing 30 and enters the housing through an aperture or slot (not shown).

The slider body 114 has two cylindrical throughbores 130 or tube-like structures affixed thereto through which the fixedly mounted guide rails 112 are received. The guide rails 112 are mounted to the top or to the side of the housing 30 so that the slider body 114 slides vertically along the guide rails 112. Since the lower platform support arm 98 is rigidly affixed to the slider body 114, the lower platform support arm and the lower platform 96 move in unison with the slider body.

Note that the scale support arm 120 is attached to the slider body through a bridge member 132. The bridge member 132 provides a rigid mechanical link so that the lower platform 96 and corresponding scale support arm 120 can move in an unobstructed manner. The scale support arm 120 is rigidly attached to the bridge member 132, and supports the scale 116 in a fixed relationship relative to the slider body 114. Thus, when the slider body 114 is vertically displaced, the lower platform 96 and the measuring scale 116 move simultaneously and always maintain their relative positions. Since the measuring scale 116 is operatively connected to the lower platform 96, vertical displacement of the lower platform causes corresponding vertical displacement of the scale such that the scale always measures the pupillary height 12 of the eye 16 relative to the bottom edge of the spectacle frame 20 when the lower platform 96 engages the bottom edge of the spectacle frame.

The measuring scale 116 may be a transparent ruler-like vernier with millimeter markings or gradations engraved or printed on its surface. The measuring scale 116 is disposed toward the distal end 34 of the housing 30 so that it is proximal the target aperture 36 and proximal the eye 16 of the patient 18. Note that the measuring scale 116 is essentially a vertical extension of the lower platform 96. The millimeter engravings on the measuring scale 116 begin at twenty millimeters since the lowest end of the measuring scale disposed within the housing is always twenty millimeters in height above the lower platform 96. In this way, once the lower platform 96 is positioned against the lower edge of the spectacle frame 20, the measuring scale 116 will always indicate the pupillary height 12 relative to the lower edge of the spectacle frame.

Proximity of the scale 116 toward the eye 15 of the patient 18 substantially reduces or eliminates parallax error since the optician 45 views the center of the eye 18 through the eye-piece 44 located at the other end (proximal end 32) of the housing 30. Thus, when the pupillary height 12 is measured against the measuring scale 116, as will be described in greater detail hereinafter, almost no viewing angle error exists since the scale 116 is disposed proximal to the eye 16.

The slider body 114 is fixedly attached to the toothed rod 108 which operatively engages the crown wheel 106 (FIG. 5). The toothed rod 108 and crown wheel 106 function like a worm gear and crank so that when the crown wheel is rotated, the toothed rod and hence, the slider body 114, are correspondingly vertically displaced. The adjustment knob 94 (FIG. 1) is directly connected to the crown wheel 106 external to the housing 30 so that the optician 45 can perform the adjustment. The adjustment knob 94 is disposed on the external surface of the housing 30 and permits the optician 45 to conveniently and precisely control the vertical position of the lower platform 96. Note that there are two adjustment knobs 94 disposed on opposite sides 93 of the housing 30 to permit independent control of the left and right side lower platforms 96.

The electrical wiper 122 or electrical contact (FIG. 5) is fixed to the scale support arm 120 and is configured to engage exposed electrical contacts 150 on the printed circuit board 126 which is mounted against the side of the housing 30. When the lower platform 96 and the measuring scale 116 are vertically displaced, the wiper 122 makes electrical contact at varying positions along the printed circuit board 126. The printed circuit board 126 may contain resistive elements or may contain a series of contact points such that contact therewith can be sensed by a microprocessor or by discrete logic components, as is known in the art. Thus, information corresponding to the vertical position of the measuring scale 116 is available to electrical components so that a digital readout of the pupillary height 12 can be displayed in addition to visual observation of the measuring scale, as will be described below. A paper copy of the measured parameters may also be provided. Note, to obtain pupillary height based upon the wiper 122 position, additional information, such as the point where the center of the pupil intersects the measuring scale 116, is required, as will be described hereinafter. A display device (not shown) provides a digital readout or other visual indication of the pupillary height 12 and may be incorporated into the housing 30. Alternately, the display device may be external to the housing.

Referring now to FIGS. 1, 2, 5, and 6, FIG. 6 is an enlarged detailed illustration of a horizontal reference marker mechanism 160 shown from within the housing 30. Note that two horizontal reference marker mechanisms 160 exist, each disposed on opposite lateral sides 93 of the housing 30 and directed to measuring the pupillary height 12 of the left and right eyes 16, respectively. Each horizontal reference marker mechanism 160 is independently adjustable relative to the other to facilitate measurement of the pupillary height 12 of each eye 16 independently. Also note that with respect to FIGS. 5 and 6, that both the lower platform mechanism 92 and the horizontal reference marker mechanism 160 exist adjacent to each other on each side of the housing, as shown in FIG. 2, but are shown separated for purposes of illustration only in FIGS. 5 and 6, respectively. Thus, the left side of the housing 30 includes a lower platform mechanism 92 and a horizontal reference marker mechanism 160 while the right side of the housing includes identical elements.

The horizontal reference marker mechanism 160 includes an adjustment knob 170 (FIGS. 1 and 6) or slider knob, guide rails 172, a slider body 174, a marker needle 180, an electrical wiper 182, and a printed circuit board 184. The function of the horizontal reference marker mechanism 160 is to vertically displace the marker needle 180 until it is in alignment with and intersects the center of the pupil of the eye 16. The marker needle 180 is adjacent the measuring scale 116 such that the intersection thereof can be observed by the optician 45. The position on the measuring scale 116 intersected by the marker needle 180 represents the measurement of pupillary height 12.

The marker needle 180 is a rigid metal needle or other thin marking structure rigidly affixed to the slider body 174 at substantially ninety degrees. The marker needle 180 always remains parallel to the bottom of the housing 30 as the slider body 174 is vertically displaced. The slider body 174 has two cylindrical throughbores 190 or tube-like structures affixed thereto through which the fixedly mounted guide rails 172 are received. The guide rails 172 are mounted to the top or to the lateral side of the housing 30 and are similar to the guide rail and slider of the lower platform mechanism 92. The slider body 174 is configured to slide vertically along the guide rails 172. Since the marker needle 180 is rigidly affixed to the slider body 174, it moves in unison therewith.

The adjustment knob 170 is disposed on the outside of the housing 30 and is connected to the slider body 174 through a slot 196 (FIG. 6) disposed in the side of the housing 30. The adjustment knob 170 is essentially a slide knob which the user displaces vertically to displace the marker needle 180.

The marker needle 180 is adjacent the measuring scale 116 and is disposed just behind the scale 116 where the scale is preferably transparent. Since both the measuring scale 116 and the marker needle 180 are adjacent to each other and are both disposed toward the eye 16 of the patient 18, parallax error is substantially reduced or eliminated. Virtually no angular error is induced when the marker needle 180 is aligned with the corneal reflection of the eye 16. The measuring scale 116 is disposed at a fixed distance above the top surface of the lower platform 96, preferably 20 millimeters. Accordingly, the measuring scale 116 will be graduated starting with 20 millimeters, which represents the separation between that particular graduation line and the top surface of the lower platform 96. Another way of visualizing this is to imagine a scale mounted vertically on the top surface of the platform 96 which is graduated in an upward direction. The zero point of the scale 116 coincides with the top surface of the lower platform 96 such that the portion between 0 millimeters and 19 millimeters of the scale is cut-off. The remainder is represented as a scale 116 which begins at 20 millimeters. This point is actually 20 millimeters above the platform 96. Since the top surface of the platform engages the lower eye wire of the spectacle frame, the graduation line located at 20 millimeters is also 20 millimeters from the bottom edge of the spectacles. Similarly, the graduation line of the scale 116 that coincides with the reference marker represents the actual height of the reference marker from the bottom edge of the spectacle frame. If the reference marker 180 is aligned with the corneal reflection, this distance represents the desired pupillary height measurement 12, which the optician can read directly from the scale.

The electrical wiper 182 is fixed to the slider body 174 and engages exposed electrical contacts 200 on the printed circuit board 184 which is mounted to the side of the housing 30. When the slider body 174 is displaced, the wiper 182 makes electrical contact at varying positions along the printed circuit board 184. The printed circuit board 184 may contain resistive elements or may contain a series of contact points such that contact therewith may be sensed by a microprocessor or by discrete logic components, as is known in the art. Thus, information corresponding to the vertical position of the slider body and hence, the marker needle 180 is available to the electrical components or processor.

With the position of both electrical wipers 182 and 122 determined by the electronics of the apparatus 10, a difference in position can be calculated, as is described in greater detail hereinafter. The difference in wiper 122 and 182 positions represents the difference in position between the marker needle 180 and the absolute position of the scale 116. This distance represents the pupillary height 12 and may be displayed in digital format or may be determined by visual observation. Digital display of the pupillary height 12 may be performed in addition to or to the exclusion of visual observation of the measuring scale 116. A paper copy may also be produced, as is known in the art.

Consider graduating the electrical contacts on the printed circuit boards 184 and 126 by setting them exactly one millimeter apart, similar to a scale or vernier. Preferably, there are 20 contacts and 20 graduations on each printed circuit board such that graduation No. 1 through graduation No. 20 correspond to contact No. 1 through contact No. 20. That means that when the wiper is, for example, in contact with contact No. 8, the electronics of the instrument is provided with the number 8 or the value 8, which corresponds to the exact distance in millimeters that the wiper is away from contact No. 0. In other words, the electronics of the instrument is provided with the same number or digit as the contact number of the wiper. The graduations preferably range from 0–20 as the printed circuit board 184 is viewed from bottom to top.

In the printed circuit board 126, the graduations range from 1–20 as viewed from top to bottom. These graduations are also exactly one millimeter apart. Consider an imaginary reference line (referred to as the "zero line"), which coincides with the graduation mark No. 20 of the scale/vernier 116 when the platform 96 is disposed at its lowest position. Since graduation mark No. 20 of the scale 116 is exactly 20 millimeters above the top surface of the lower platform 96, the zero line also is 20 millimeters above the platform 96 at this lowest position. The "zero line" is stationary and does not move. This same position of wiper 122 coincides with the bottom-most contact (graduation No. 20) of the printed circuit board 126, and hence it provides the digit 20 or the value 20 to the electronics of the instrument. The value of 20 is the actual separation in millimeters between the zero line and the top surface of the lower platform 96 at its lowest position. When the platform is moved upwards for example, by 5 millimeters, graduation No. 20 of the scale 116 would need to move upwards 5 millimeters from the zero line. Since the zero line is stationary, the platform 96 is currently 15 millimeters (20-5) below the zero line. Additionally, the wiper 122 would need to move from contact No. 20 to contact No. 15, and hence it provides the number or value 15 to the electronics of the apparatus 10. Similarly, the value of 15 is the actual separation in millimeters from the top surface of the platform 96 and the zero line. Since graduation No. 20 of scale 116 is 5 millimeters above the zero line, the platform is actually 15 millimeters below the zero line. Such information is available to the electronics of the apparatus 10.

Similarly, when the reference marker 180 is moved to its lowest position, it coincides with the zero line. At this position, the wiper 182 coincides with contact No. 0 located at the bottom of the printed circuit board 184. When the reference marker 180 is raised, for example, by 8 millimeters, it will be 8 millimeters above the zero line. Wiper 182 will then be disposed against contact No. 8, and hence will provide the value of 8 to the electronics of the apparatus. The exact distance in millimeters from the platform 96 to the zero line is provided by printed circuit board 126. Similarly, the exact distance in millimeters from the zero line to the reference marker 180 is provided by the printed circuit board 184. The electronic components (not shown) of the apparatus add the two readings and display the sum, since that value represents the desired separation between the top surface of the platform 96 and the reference marker 180.

Referring now to FIGS. 1-3, in operation, the housing 30 is secured to the patient 18 such that the patient is directed to look into the target apertures 36 of the housing. Note that the pupillary height 12 for each eye is measured independently using the below-described method. The flexible band 46 is fitted and secured about the forehead of the patient 18 and the optician 45 adjusts the upper guide adjustment knob 62 until the planar shelf 56 engages the upper edge of the patient's spectacle frame 20. This prevents the spectacle frame 20 from inadvertently becoming displaced relative to the housing 30. Next, the optician 45 turns on the apparatus to illuminate the internal lamp 74 and directs the patient 18 to focus on the light source. The optician 45 then looks into the eye-piece 44 and observes the patient's eyes 18.

Next, the optician 45 turns the lower platform adjustment knob 94 to displace the lower platform 96 from the position shown by reference letter "A" (FIG. 1) to the position shown by reference letter "B". This causes the lower platform 96 to engage the lower edge of the spectacle frame 20 so that the spectacle frame is bounded between the upper guide 56 and the lower platform. The optician 45 then aligningly views the corneal refection of the patient's eye through the eye-piece 44 and slides the reference marker adjustment knob 170 until the marker needle 180 is at the exact center of the corneal reflection.

The optician 45 then reads the point on the measuring scale 116 where the marker needle 180 intersects the measuring scale and makes note of the measurement. This measurement represents the pupillary height 12 as measured from the bottom of the spectacle frame 20 to the center of the patient's pupil, as indicated by the corneal reflection. This procedure is performed for the left eye and the right eye.

Note that the spectacle frames 20 may have a particular thickness if it fully encloses the lenses 22 or alternately, may have no thickness at the bottom of the lenses if the frame is affixed to the lenses only at the top portion of the lenses (rimless frames). An offset switch (not shown) may be connected to the printed circuit boards 126 and 184 which corresponds to the type of spectacle frames worn by the patient 18. Most plastic frames have a thickness of about 2.0 millimeters and an inside bevel of about 0.5 millimeter, while metal frames have a total thickness of about 1.0 millimeters and an inside bevel of about 0.5 millimeters. Depending upon the selection of the offset switch, the estimated thickness of the frames 20 may be automatically subtracted from the pupillary height 12 measurement to yield a more accurate reading. Obviously, if the optician 45 is reading the measurement from the measuring scale 116 without benefit of a digital display, the optician 45 can easily perform the subtraction mentally.

Figure 7:
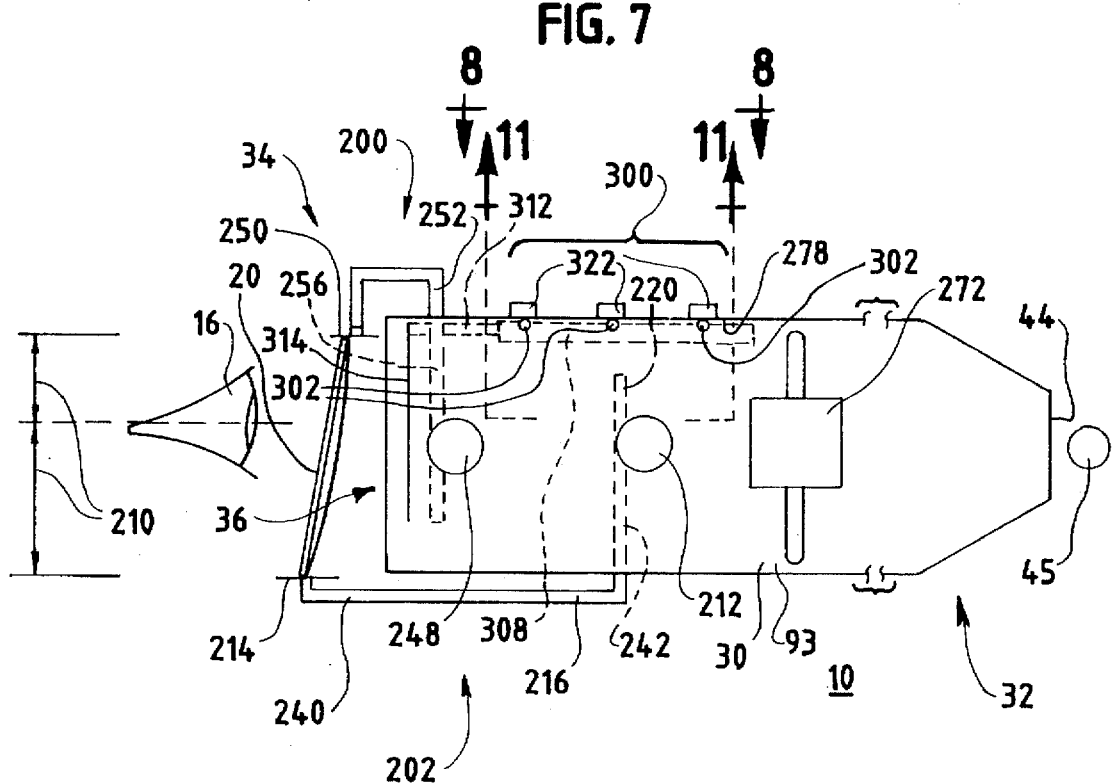
FIG. 7 is a side elevational view of an alternate embodiment illustrating a combination horizontal decentration and vertical decentration measuring apparatus.

Referring now to FIGS. 7-10, an alternate embodiment of the apparatus 10 for measuring pupillary height and pupillary decentration is shown generally in FIG. 7. Like reference numerals will be used to show similar structures.

The apparatus 10, in the alternate embodiment, is similar to the apparatus shown in FIGS. 1-2 but includes a mechanism for measuring pupillary distance (PD) in addition to the mechanism for measuring pupillary height. The alternate embodiment described not only combines two devices, namely a PD measuring apparatus and pupillary height measuring apparatus, into one device, but also directly provides the horizontal and vertical decentration which are presently calculated manually from the combination of the measured PD, the pupillary height, and the frame dimensions. Note, that all references to the width of the spectacle frame 20 or references to the left and right edges of the spectacle frame are referring to measurements of a single half or a single lens portion of the frame. The term "width" does not refer to the full width across both lens of the frame 20. FIGS. 7-10 illustrate an upper platform mechanism 200, a lower platform mechanism 202, and a horizontal reference marker mechanism 204, generally. The upper platform mechanism 200 and the lower platform mechanism 202 are similar to each other and are also similar to the lower platform mechanism 92 shown in FIG. 5.

Also note that the upper and lower platform mechanisms 200 and 202 are disposed adjacent each other and such identical mechanisms are disposed on opposite lateral sides 93 of the housing 30. The upper and lower platform mechanisms 200 and 202 and horizontal reference marker mechanism 204 disposed on the left lateral side of the housing 30 are directed toward measuring a vertical decentration 210 (FIG. 7) of the left eye of the patient while the identical mechanisms disposed on the right lateral side of the housing are directed toward measuring the vertical decentration of the right eye. The lower platform mechanism 202 associated with each eye 16 is independently adjustable relative to the lower platform mechanism associated with the other eye. This facilitates independent measurement of the vertical decentration 210 of each eye. The upper platform mechanism 200 associated with the left and right portions of the device 10 are similarly independently adjustable.

Figure 8:
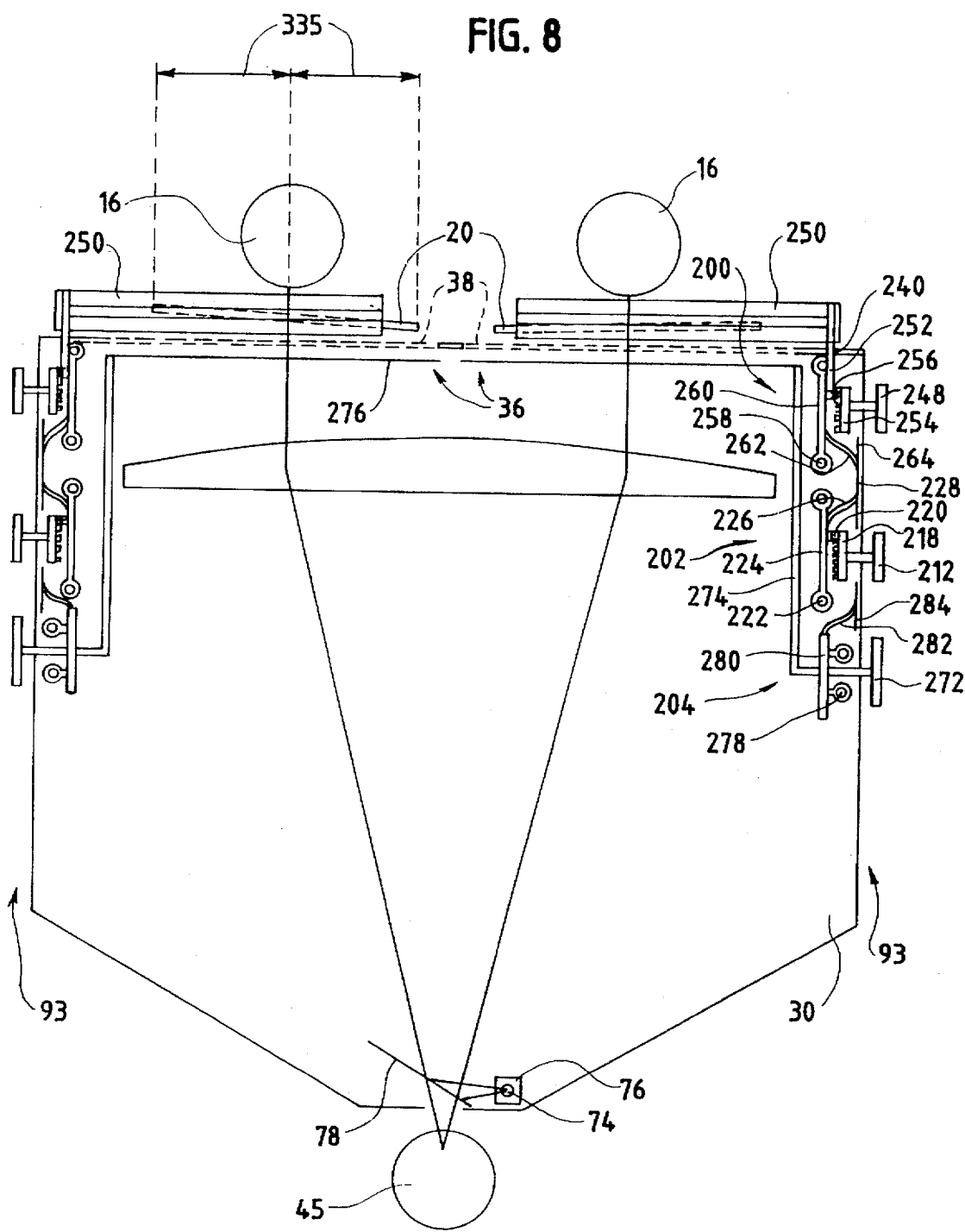
FIG. 8 is a top plan sectional view of a combination horizontal and vertical decentration measuring apparatus, taken along the line 8—8 of FIG. 7 in the direction generally indicated.
Figure 9:
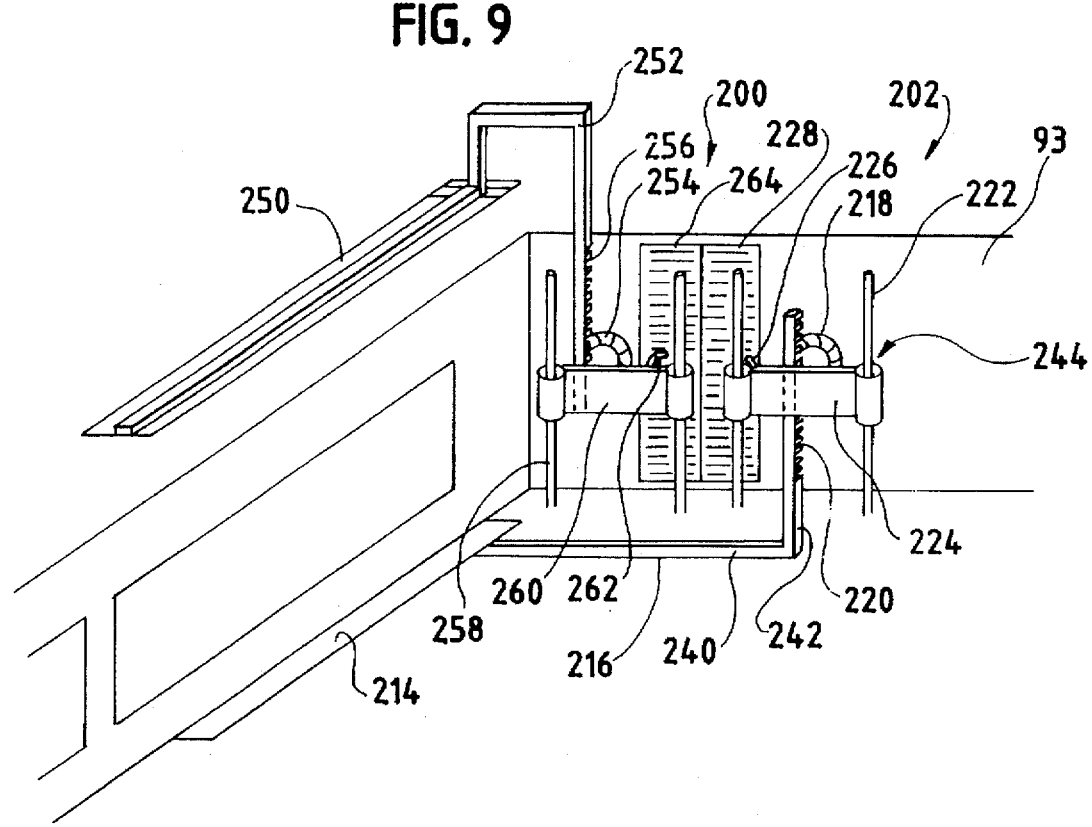
FIG. 9 is an enlarged perspective view of an upper and lower platform mechanism shown in FIG. 8.

The lower platform mechanism 202 includes a lower platform adjustment knob 212 (FIGS. 7 and 8), a lower platform 214 (FIGS. 7 and 9), a lower platform support arm 216 (FIGS. 7 and 9), a crown wheel 218 (FIGS. 8 and 9), a toothed rod 220, a pair of guide rails (FIGS. 8 and 9), a lower platform slider body 224 (FIGS. 8 and 9), an electrical wiper 226 (FIGS. 8 and 9), and a printed circuit board 228 (FIGS. 8 and 9). The function of the lower platform mechanism 202 is to displace the lower platform 214 in a vertical direction until the lower platform engages the bottom rim of the patient's spectacle frame 20 (FIG. 7). Accordingly, the lower platform 214 is external to the housing 30 and is supported by the lower platform support arm 216 which extends outside the housing but enters the housing through an aperture (not shown) or slot in the bottom of the housing. The horizontal portion 240 is disposed substantially external to the housing 30 and extends away from the housing to permit the lower platform 214 to be displaced vertically until it contacts the lower edge of the spectacle frame 20. The lower platform support arm 216 is formed from the horizontal portion 240 and a vertical portion 242 connected to the horizontal portion at substantially ninety degrees. Upper reaches of the vertical portion 242 terminate forming the toothed rod 220.

The lower platform slider body 224 (FIG. 9) has two cylindrical throughbores 244 or tube-like structures affixed thereto through which the fixedly mounted guide rails 222 are received. The guide rails 222 are mounted on the side or to the bottom of the housing 30 so that the lower platform slider body 224 slides vertically along the guide rails. Since the lower platform support arm 216 is rigidly affixed to the lower platform slider body 224, the lower platform support arm and the lower platform 214 move in unison with the slider body. Thus, when the lower platform support arm 216 is vertically displaced by rotation of the lower platform adjustment knob 212, the lower platform 214 is correspondingly displaced to contact the bottom edge of the spectacle frame 20.

The upper platform mechanism 200 is substantially identical to the lower platform mechanism 202 and includes an upper platform adjustment knob 248 (FIGS. 7 and 8), an upper platform 250 (FIGS. 7 and 9), an upper platform support arm 252, a crown wheel 254, a toothed rod 256, a pair of guide rails 258, an upper platform slider body 260, an electrical wiper 262, and a printed circuit board 264. The function of the above delineated structures are substantially identical to the corresponding structures associated with the lower platform mechanism 202. Accordingly, when the upper platform adjustment knob 248 is rotated, the upper platform 250 is adjusted to contact the upper edge of the spectacle frame 20.

Figure 10:
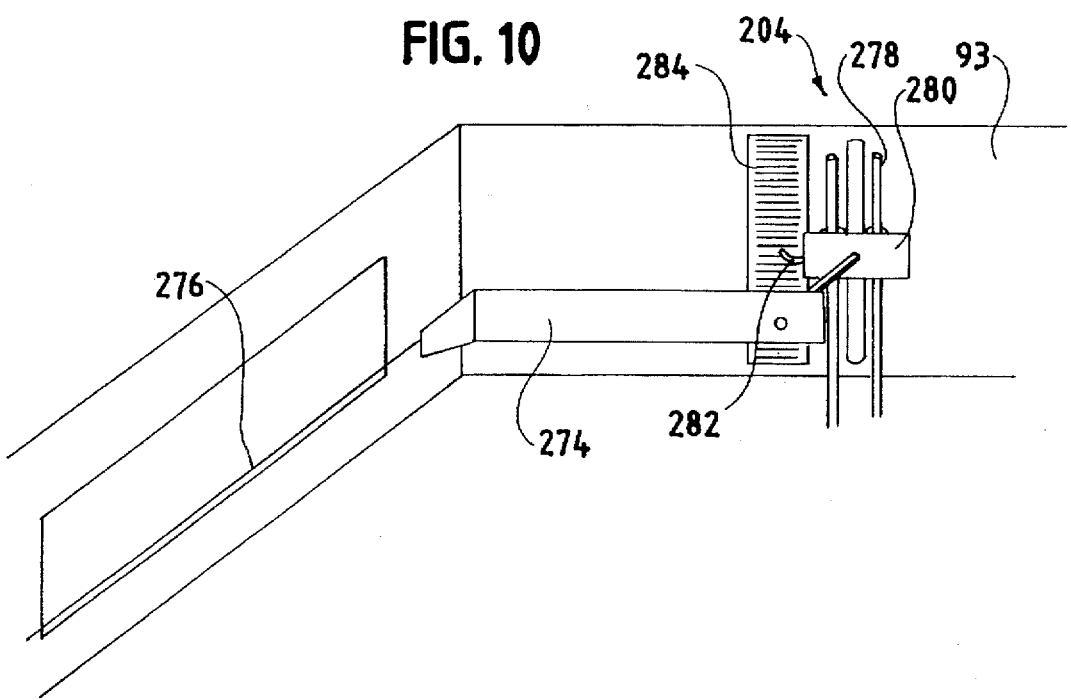
FIG. 10 is an enlarged perspective view of a horizontal reference marker mechanism shown in FIG. 8.

Referring now to FIGS. 7–10, FIG. 10 illustrates the horizontal reference marker mechanism 204. The horizontal reference marker mechanism 204 is very similar to the upper platform mechanism 200 and the lower platform mechanism 202 shown in FIG. 9. The horizontal reference marker mechanism 204 includes an adjustment slider knob 272, a horizontal reference marker support arm 274, a horizontal reference needle 276, a pair of guide rails 278, a reference marker slider body 280, an electrical wiper 282, and a printed circuit board 284. The horizontal reference marker mechanism 204 is shown in FIG. 10 separated from the upper and lower platform mechanisms 200 and 202 of FIG. 9 for purposes of clarity only. In the novel device 10, the upper platform mechanism 200, the lower platform mechanism 202, and the horizontal reference marker mechanism 204 are disposed proximal each other on each lateral side 93 of the device 10. Each lateral side 93 of the device 10 includes the same three mechanisms 200, 202, and 204, but directed toward corresponding eyes 16 of the patient.

The upper platform 250, the lower platform 214, and the horizontal reference needle 276 operate in conjunction with each other to provide a measurement of vertical decentration 210 (FIG. 7). When the upper platform 250 and the lower platform 214 contact the upper and lower edges of the spectacle frame 20, respectively, the electrical wipers 262 and 226 contact exposed electrical contacts on the corresponding printed circuit boards 264 and 228, which are mounted against the side of the housing 30.

After the upper and lower platforms 250 and 214 are positioned against the upper and lower edges of the spectacle frame 20, respectively, the horizontal reference needle 276 is vertically adjusted by the sliding adjustment knob 272 to be aligned with and intersect the center of the pupil of the eye 16, via observation of the corneal reflection. Thus, the wipers 262, 226, and 282 all contact corresponding printed circuit boards 264, 228, 284 permitting measurement of the position of the horizontal reference needle 276 relative to the upper platform 250 and the lower platform 214, as described in greater detail hereafter. The function of the printed circuit boards 228, 264, and 284 and the wipers 262, 226, and 282 is similar to the function of the printed circuit boards and wipers disclosed with respect to FIGS. 1–6. Accordingly, the microprocessor or other discreet electronic components (not shown) receives the wiper position information and calculates the vertical decentration with respect to the top and bottom of the spectacle frame 20.

In this alternate embodiment illustrated in FIGS. 7–10, vertical decentration 210 (FIG. 7) is defined as the vertical distance from the center of the pupil (corneal reflection) to the vertical midpoint of the frame 20, and may be a positive or a negative value that is assigned, depending upon whether the center of the pupil is above or below the vertical midpoint of the frame. If only a single measurement, namely the pupillary height from the center of the pupil to the lower edge of the spectacle frame 20 were provided, the optician would need to perform an additional calculation to determine the vertical decentration in the following manner. The optician would divide the height of the spectacle frame 20 by two to obtain the vertical midpoint and then subtract that value from the pupillary height to obtain the vertical decentration. This is an inefficient and time-consuming step that is eliminated in the illustrated alternate embodiment.

Accordingly, since the present novel device 10 includes top and bottom platforms 250 and 214 to locate and fix the position of the top and bottom edges of the spectacle frame 20, the electronic components (not shown) operatively coupled to the electrical wipers 262, 226, and 282 calculate the relative position of the center of the pupil with respect to the vertical midpoint of the spectacle frame, and provides the result as either a positive or negative value representing the vertical decentration 210 (FIG. 7). Such a calculation is extremely advantageous to the optician 45. However, a single partial measurement of pupillary height, such as could be provided by the horizontal reference needle 276 and either of the two platforms 214 and 250 and associated mechanisms 200 or 202, may also be used.

Figure 14:
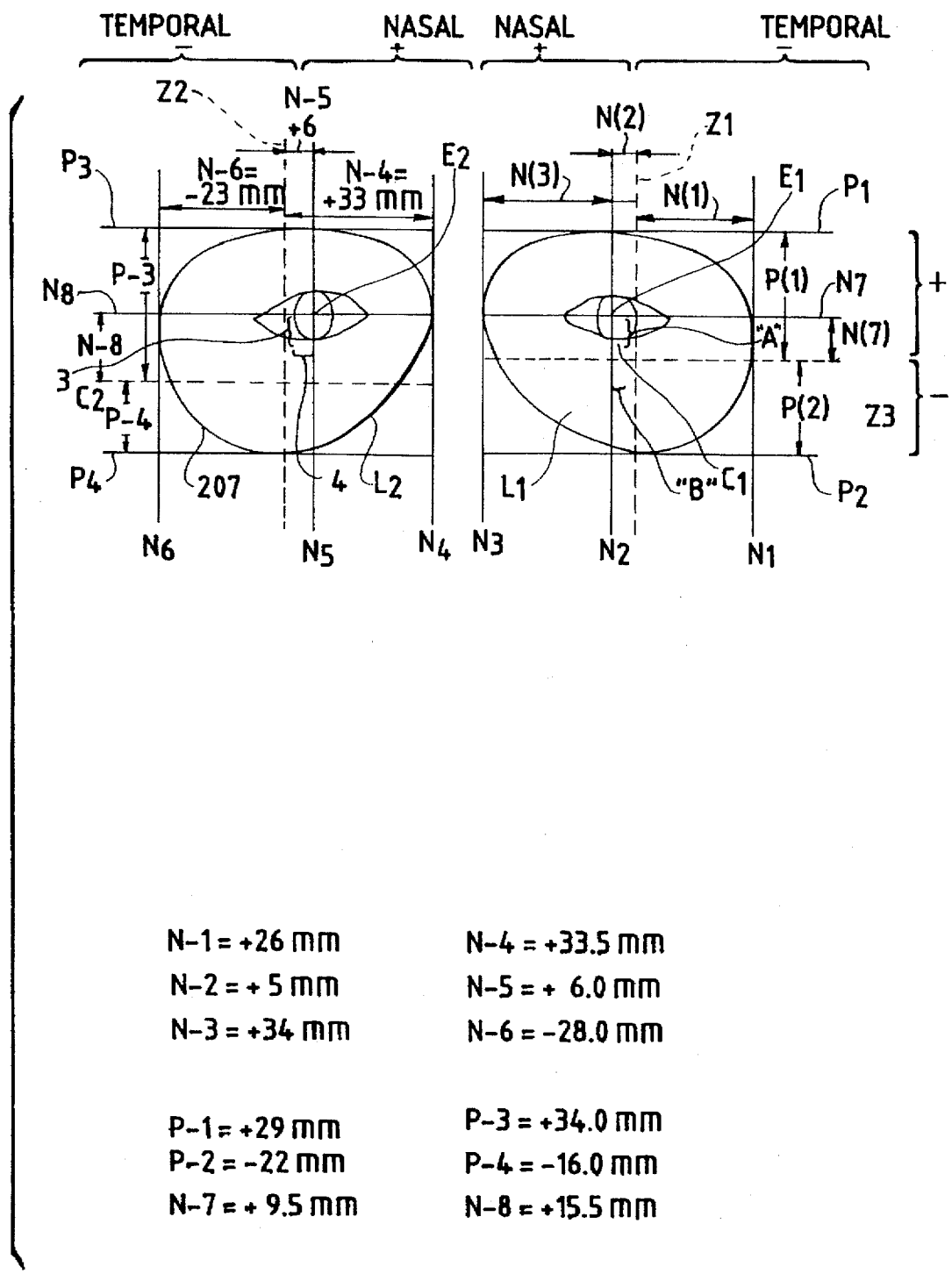
FIG. 14 is a front schematic view illustrating calculation of measured parameters.

Now referring to FIGS. 9 and 14, since upper and lower platforms 214 and 250 and the horizontal reference 276 marker are all movable, a stationary zero line (FIG. 14) may be established. The upper platform mechanism 200 is constructed such that when the upper platform 250 is located at the zero line Z3, wiper 262 is located at the bottom-most contact on the printed circuit board 264. Alternately, when wiper 262 is located at the bottom most contact on the printed circuit board 264, the upper platform 250 is, for example, 10 millimeters above zero line Z3. In this situation, the bottom-most contact contacts the wiper 262 at this position, and provides a measurement of 10 millimeters to the electronics of the device. Preferably, all of the contacts on the printed circuit board 264 are set 0.5 millimeters apart and the graduations range from 10 millimeters to 35 millimeters as the printed circuit board is viewed from bottom to top. When the first contact of the wiper is contacted at this position, the printed circuit board provides a measurement of 10 millimeters to the electronics of the device. When the upper platform is moved upwards from that position, the contacts in contact with the wiper at each half millimeter point provide the actual distance that the upper platform 250 is away from the zero line Z3. All measurements above the zero line are denoted to be positive.

Similarly, with respect to the lower platform mechanism 202, when the wiper 226 is at the top-most contact, for example, the lower platform 214 is 10 millimeters below the zero line Z3. In this case, the wiper 226 engages the upper most contact of the printed circuit board 228 and provides a measurement equal to −10 millimeters. All contacts on printed circuit board 228 are set 0.5 millimeters apart while the graduations range from 10 millimeters to 35 millimeters as the printed circuit board is viewed from top to bottom. When the lower platform is moved downwards from this position, the contacts in contact with the wiper at each half millimeter point convey the actual distance that the lower platform is away from the zero line Z3. All measurements below the zero line Z3 are denoted to be negative.

In the case of the horizontal reference marker moving mechanism 204, when the wiper 282 engages, for example, the middle of the printed circuit board 284, the horizontal reference marker 276 coincides with the zero line Z3. The contact between contact No. 0 located in the middle of the printed circuit board 284, and the wiper 282 provides a measurement of zero millimeters to the electronics of the device. All of the contacts on printed circuit board 284 are set 0.5 millimeters apart and are graduated upwards (0 to +10) from the contact No. 0 as the board is viewed from bottom to top, and are graduated downwards (0 to −10) from the contact No. 0 as the board is viewed from top to bottom. If the horizontal reference marker 276 is moved upward from the zero line, the contacts at each half millimeter point convey the exact number of millimeters that the reference marker 276 is above the zero line Z3. Similarly, if the reference marker 276 is moved down from the zero line Z3, the contacts at each half millimeter point convey the exact distance it is away from the zero line. Upward movements from the zero line Z3 are denoted as a positive value and downward movements are denoted as a negative value.

Referring now to FIG. 14, a numerical example for the calculation of vertical decentration follows. In FIG. 14 lines P1, P2 and N7 denote the positions of the upper platform 250, the lower platform 214, and the horizontal reference marker 276, respectively. Line P1 is 29 millimeters above the zero line Z3 and, therefore the separation between lines Z3 and P1, referred to as P(1), is equal to +29 millimeters. Line P2 is 22 millimeters below Z3 and, therefore the separation between line Z3 and P2, referred to as P(2), is equal to −22 millimeters. Similarly, line N7 is 9.5 millimeters above line Z3 and therefore, the separation between lines Z3 and N7, referred to as N(7) is equal to +9.5 millimeters. The vertical decentration (reference letter "A" in FIG. 14) is derived using the following formula, which may be incorporated into the electronics of the device.

$$\text{Vertical decentration} = N(7) - \frac{(P(1) + P(2))}{2}$$
$$= 10\,\text{mm} - +29\,\text{mm} + (-21\,\text{mm}))$$
$$= +6\,\text{mm}$$

Vertical decentration equal to +6 millimeters means that the pupil of the eye is displaced 6 millimeters above the vertical midpoint of the frame.

If only a measurement of the pupillary height is desired, the electronics of the device may calculate the pupillary height as follows.

$$\text{Pupillary height} = N(7) - P(2)$$
$$= 10\,\text{mm} - (-21\,\text{mm})$$
$$= +31\,\text{mm}$$

Referring now to FIGS. 7 and 8, in operation, the housing 30 is secured to the patient who is wearing the selected spectacle frames 20. The optics of the device 10 shown in FIG. 8 are similar to the embodiment shown in FIG. 2 with various similar reference numerals omitted for purposes of clarity. The optician 45 then rotates the upper platform adjustment knob 248 to vertically displace the upper platform 250, causing the upper platform to contact the upper edge of the spectacle frame 20. Next, the optician 45 performs the same operation with respect to the lower platform 214 so that the spectacle frame 20 is bounded between the upper platform 250 and the lower platform 214.

The optician 45 then aligns the corneal reflection of the patient's eye 16 through the eyepiece 44 and slides the horizontal reference marker adjustment knob 272 until the horizontal reference marker needle 276 is at the exact center of the corneal reflection. The optician 45 then depresses a button (not shown) which saves the measurement of vertical decentration for later viewing or subsequent transfer to paper using a suitable commercially available printer, as is known in the art. The same operation is then performed for the opposite eye 16. Horizontal and vertical decentration measurements may be completed for each eye and may be performed before corresponding measurements for the other eye are obtained. Alternately, measurements of vertical decentration for both the right eye and the left eye may be obtained before measurements of horizontal decentration are obtained. This is in accordance with the optician's 45 preference.

Figure 11:
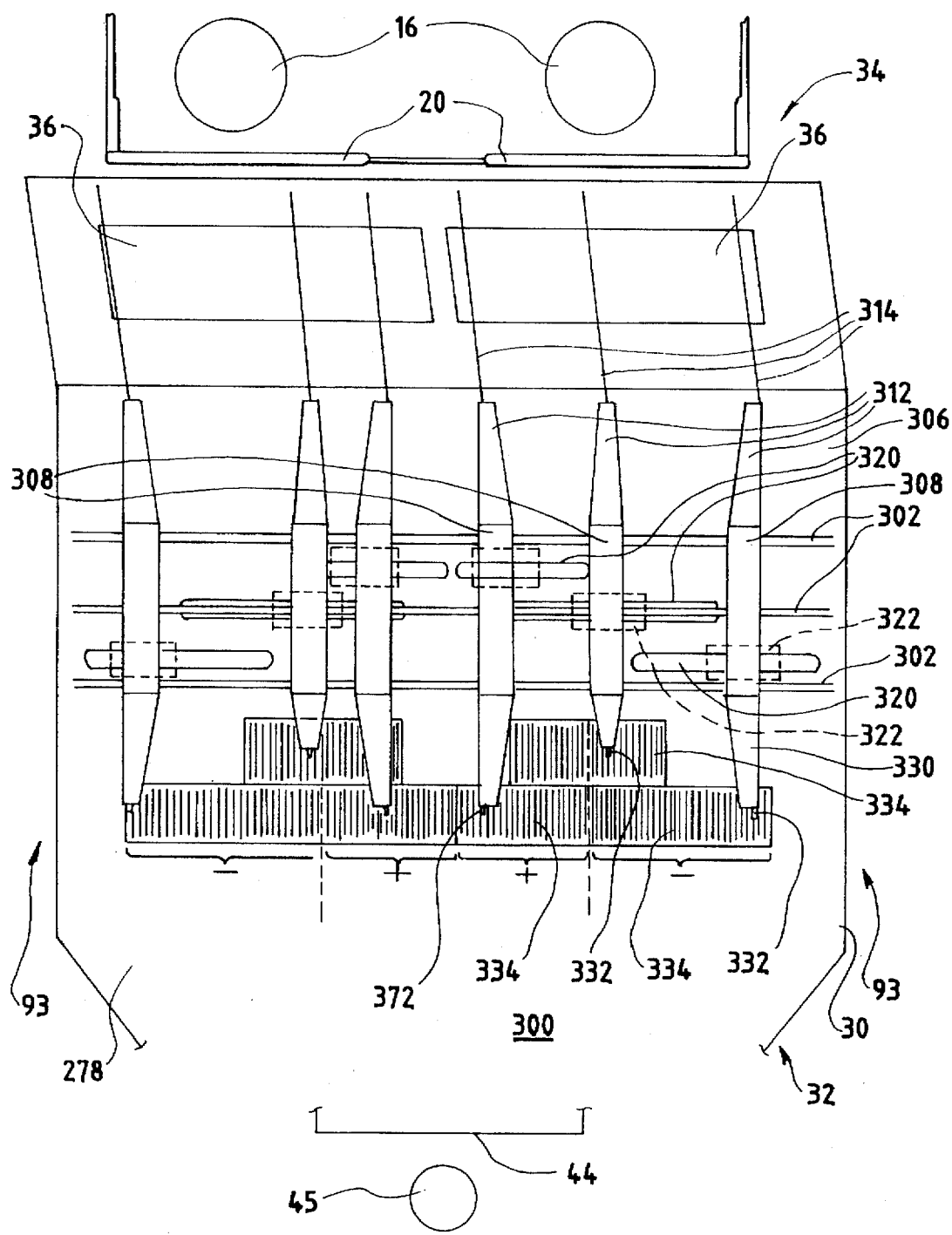
FIG. 11 is an inverted plan view of an inside cover of the apparatus, taken along the line 11—11 of FIG. 7 in the direction generally indicated, particularly showing the vertical reference marker mechanism.

Referring now to FIGS. 7 and 11, FIG. 11 illustrates an inverted top view of an inside portion 278 of the top of the enclosure 30, which is directed generally toward a decentration mechanism 300. FIG. 11 illustrates the inside portion 278 of the enclosure 30 in an inverted position in order to view the inside surface upon which the decentration mechanism 300 is disposed. In FIG. 11, reference numerals for only the right-hand lateral side 93 are shown for purposes of clarity only.

The decentration mechanism 300 for a single lateral side 93 includes three spaced-apart parallel slide rails 302 that extend between the opposite lateral sides. The slide rails 302 are disposed on the top inside portion 278 of the enclosure 30, thus the side rails are only shown in detail when viewed from the direction indicated by line 11—11 of FIG. 7.

Six identical slider plates 308 are mounted on the slider rails 302 and freely slide in a lateral direction within a predetermined range, as will be explained in greater detail hereinafter. All slider plates 308 are identical to each other and are grouped into two sets of three slider plates where the three left-most slider plates correspond to the left eye measurement of decentration, and the three right-most slider plates correspond to the right eye measurement of decentration. The slide rails 302 and the slider plates 308 may be similar in configuration to the guide rails 222 and slider body 224 shown in FIGS. 8 and 9. However, any suitable configuration permitting the slider plates 308 to freely slide along the slide rails 302 may be used. Each slider plate 308 is slidingly held in place parallel to the top inside portion 278 by the three slide rails 302 received through each slider plate.

The distal end 34 of each slider plate 308 (disposed toward the target apertures 36) includes an extension portion 312 that extends from the slider plate toward the target apertures. A vertical reference needle 314 extends at right angles from the distal end 34 of each of the extension portions 312 and depends vertically downward from the extension portions such that they are generally parallel to the target apertures 36. Note that in FIG. 7, only one of the three slider plates 308, the extension portions 312, and the vertical reference needles 314 are shown for purposes of clarity only, while in FIG. 11, all slider plates are shown.

Each of the slide rails 302 is vertically disposed under, or slightly to one side of and under a slot or opening 320 in the top of the enclosure 30. The slots 320, do not extend across the full lateral width of the enclosure 30 but rather, extend across only a portion of the width of the device 10.

Decentration slide knobs 322 are disposed on the outside top surface of the enclosure 30 and are coupled to each corresponding slider plate 308. Lateral displacement of the slide knobs 322 within the range afforded by the width of the slots 320 causes corresponding horizontal or lateral movement of the vertical reference needles 314.

The proximal end 32 of each slider plate 308 includes a proximal extension portion 330 which terminates in an electrical wiper 332. Each electrical wiper 332 contacts a corresponding printed circuit board 334. The electrical wipers 332 and printed circuit boards 334 are similar to the electrical wipers and printed circuit boards shown in FIGS. 9 and 10. Again, a microprocessor or discrete electronics (not shown) operatively coupled to the printed circuit boards 334 determines the lateral position of the wipers 332 with respect to the corresponding printed circuit board 334.

Now referring to FIGS. 11 and 14, reference letter "B" in FIG. 14 represents the horizontal decentration. The vertical lines labeled N1, N2 and N3 represent the three vertical reference needles 314 for the left eye of the patient. Since all three reference needles 314 are moveable, an arbitrary imaginary stationary vertical zero line denoted as Z1 is established for that eye. When any of the three reference needles 314 coincide with the zero line Z1, their respective wipers 332 will also be located at the zero line Z1 shown as a dotted line across printed circuit board 334 in FIG. 11. If any of the three wipers is moved from the zero line Z1 toward the nasal or the temporal side, the wipers engage contacts at each half millimeter point on the printed circuit board to yield the exact number of millimeters that the wiper is away from the zero line Z1. All movements to the nasal side are denoted as positive values and movements toward the temporal side are denoted as negative values.

FIG. 14 illustrates two scenarios, one each for the left and right eye. However, only calculations for one eye will be described in detail. In the case of the left eye of the patient, the distance between lines N1 and Z1 is denoted by N(1) which equals −27 mm, the distance between lines N2 and Z1 is denoted by N(2) which equals +5 mm, and the distance between lines N3 and Z1 is denoted by N(3) which equals +34 mm. These three numbers are available to the electronics of the device which calculate the decentration using the following formula:

$$\text{Horizontal decentration} = N(2) - \frac{(N(1) + N(3))}{2}$$
$$= +5 - \frac{((-27) + (+34))}{2}$$
$$= +1.5 \text{ mm}$$

Horizontal decentration is equal to +1.5 millimeters indicating that the optical center of the lens should be moved 1.5 millimeters from the frame center C1 in FIG. 14. The sign indicates that the optical center should be moved toward the nose of the patient (nasal) if the sign is positive, and toward the temple (temporal) if the sign is negative. Typically, the nasal and temporal movements are referred to as "decentrating in" for nasal movements, and "decentrating out" for temporal movements.

Referring now to FIGS. 7–11, the distal portion 34 of each extension portion 312 extends sufficiently forward toward the target apertures 36 such that the vertical reference needles 312 are disposed parallel to and very near the target apertures 36. This substantially eliminates parallax error. The optician 45 manually displaces the vertical reference needles 314 by moving the corresponding decentration slide knob 322 disposed on the outside of the enclosure 30.

In operation, after the above-described vertical decentration measurements 210 (FIG. 7), have been obtained with reference to FIGS. 7–10, measurements of horizontal decentration 335 (FIG. 8) are obtained using the decentration mechanism 300, as will be described as follows. The optician 45 views the eye 16 of the patient through the ocular 44 and laterally displaces the left-most decentration slide knob 322 corresponding to the set of 3 slider plates 308 (which have been assigned reference numerals on the right hand lateral side 93 in FIG. 11), such that the corresponding vertical reference needle 314 is in alignment with the nasal edge of the spectacle frame 20 for the right eye of the patient. Note that the slot 320 corresponding to the left-most slider plate 308 is sufficiently wide to permit lateral movement of the vertical reference needle 314 so that it is aligned with the nasal edge of the spectacle frame 20 within a suitable range to accommodate all patients. Accordingly, the slots 320 do not extend laterally across a large portion of the width of the enclosure 30.

The optician 45 then performs the same operation using the right-most decentration slide knob 322 to align the corresponding vertical reference needle 314 with the temporal edge of the spectacle frame 20 for the patient's right eye. Next, the optician 45 uses the center decentration slider knob 322 and aligns the center vertical reference needle 314 with the corneal reflection of the eye 16 such that the center vertical reference needle is aligned with and intersects the exact center of the eye.

The position of the electrical wipers 332 with respect to the zero line yields the three parameters required for use in the formula described above. The optician 45 then depresses a button (not shown) which causes the electronics of the system 10 to calculate and save the measurement of horizontal decentration 335 (FIG. 8) for later viewing or for subsequent transfer to a hard-copy using a suitable commercially available printer, as is known in the art. Thus, the above-described procedure using the three vertical reference needles 314 permits the optician 45 to obtain a precise measurement of horizontal decentration. Note that the process is repeated for the other eye 16.

Horizontal decentration 335 (FIG. 8) is the horizontal distance from the center of the pupil (corneal reflection) to the horizontal midpoint of the spectacle frame 20, and may be assigned an arbitrarily positive or negative value, depending upon whether the center of the pupil is to the left or to the right of the horizontal midpoint of the frame. Note that if only a single measurement from the center of the pupil to one of the spectacle edges (nasal or temporal edge) is provided, the optician would need to perform an additional calculation to determine the horizontal midpoint of the spectacle frame 20. The optician would divide the width of the frame (width of the frame corresponding to one lens of the frame) by two to obtain the horizontal midpoint and then subtract that value from the horizontal distance value obtained from one of the spectacle frame edges to the center of the pupil. Again, this is an inefficient and time-consuming step that is eliminated in the illustrated alternate embodiment.

The electronic components or microprocessor (not shown) operatively coupled to the electrical wipers 332 calculate the relative position of the center of the pupil with respect to the horizontal midpoint of the spectacle frame 20 and provide the result as a positive or negative value representing the horizontal decentration. Such a calculation is extremely advantageous to the optician 45. However, a single partial measurement of pupillary distance, such as could be provided by the position of the center vertical reference needle and either of the nasal or temporal vertical reference needles for that eye. Adding one-half of the horizontal separation between the two nasal vertical reference needles to the horizontal separation of the nasal vertical reference needle and the center vertical reference needle permits the half spacing between the pupils (monocular PD) for that eye to be obtained.

Note that the vertical reference needles 314, which are mechanical in nature, may be replaced with suitable "electronic" needles. Such electronic needles provide an image of a needle or line along a transparent strip, such as along an LCD-type strip or other transparent glass or plastic strip. Thus, the optician views an image of a displayed needle and uses the corresponding knobs to electronically displace the image of the electronic needle along the LCD-type strip until proper alignment is achieved.

Figure 12:
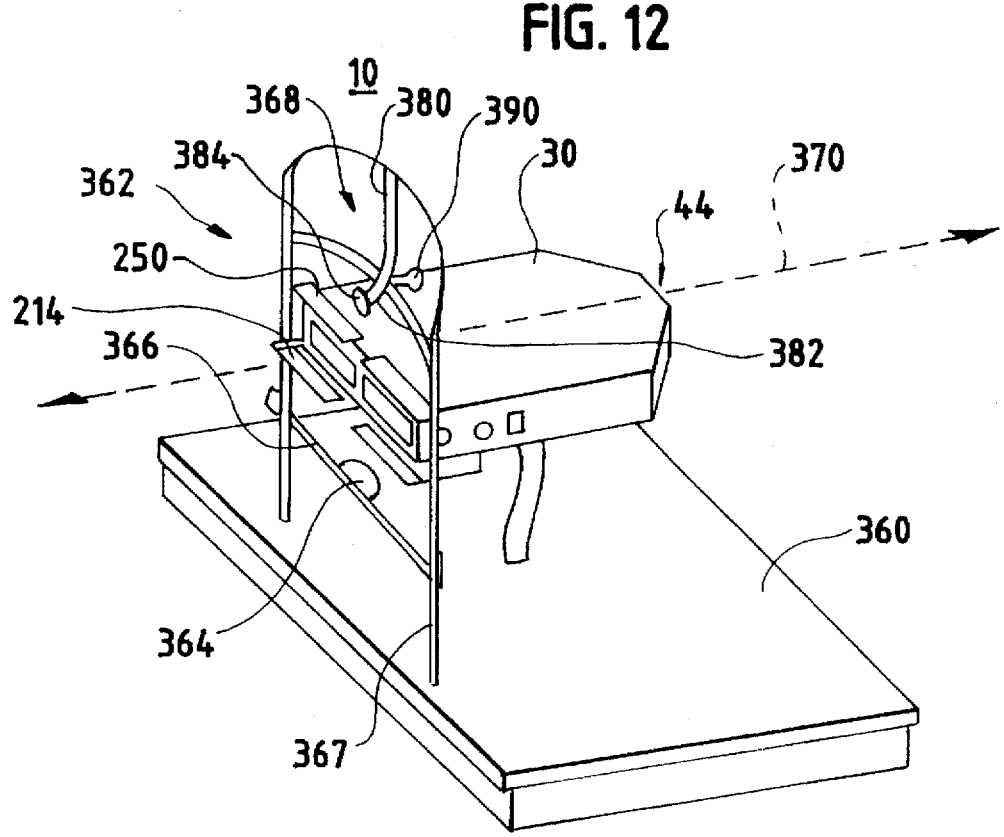
FIG. 12 is a perspective view of a specific embodiment of a horizontal and vertical decentration measuring apparatus, according to the present invention, shown in an operative position.
Figure 13:
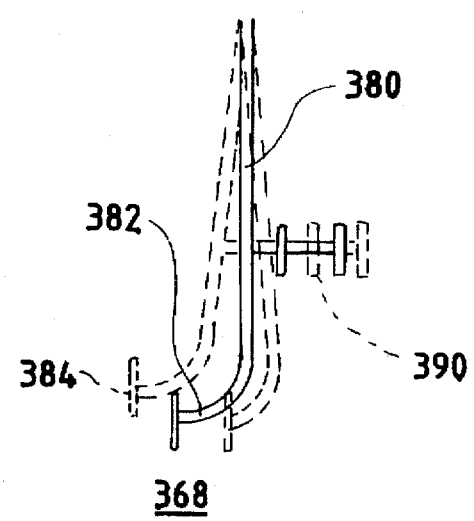
FIG. 13 is a side elevational view of an adjustment mechanism shown in FIG. 12.

Referring now to FIGS. 12 and 13, FIG. 12 illustrates the present invention 10 in an operative arrangement suitable for obtaining vertical decentration 210 (FIG. 7) and horizontal decentration 335 (FIG. 8) measurements of the patient. Preferably, the device 10 is fastened or supported on a suitable table 360 or platform in conjunction with a head positioning mechanism 362 operative to fix the position of the head of the patient relative to the device. The head positioning mechanism 362 includes a chin rest 364 which increases user comfort during the measurement process and also aids in stabilizing the position of the patient's head. The chin rest 364 is disposed on a horizontal brace 366 attached to the head positioning mechanism 362. Alternately, the chin rest 364 may be vertically displaceable along vertical support rails 367 so that it may be adjusted by the optician 45 so that the patient may view the target apertures 36 (FIG. 7) at an appropriate height relative to the housing 30.

In FIG. 13, a forehead rest 368 is illustrated. The forehead rest 368 downwardly depends from an upper portion of the head positioning mechanism 362 and is disposed along a midpoint 370 of the device 10 so as not to interfere or contact the upper platforms 250 or the lower platforms 214, respectively. The forehead rest 368 includes a vertical support portion 380 that has a curved portion 382 at its lower end. The curved portion 382 terminates with a rubber bumper or soft cushion 384 which contacts the patient's forehead to provide a suitable cushion for user comfort and for operatively fixing the position of the patient's head with respect to the device 10. The vertical support portion 380 and hence, the rubber bumper 384 are forwardly and backwardly adjustable relative to the patient's forehead.

A screw-type adjustment 390, when rotated, displaces the vertical support portion 380 such that the rubber bumper 384 contacts the forehead of the patient. In operation, the patient places his or her chin on the chin rest 364 and places the forehead against the rubber bumper 384 of forehead rest 368. Then optician 45 adjusts the screw-type mechanism 390 forward or backward so that the face of the patient is looking in a "straight ahead" fashion or is directed in a slight upward fashion (about 15 degrees). The object of the adjustable forehead rest 368 is to leave the face of the patient in a vertical orientation while the measurements are taken, and to prevent measurement errors in the vertical decentration, due to the fact that the face was overly directed or tilted upwards or downwards. Alternately, instead of a single rubber bumper 384, a three pronged rubber bumper, having two bumpers on either side of a middle bumper, may be used. This bumper is constructed in an arc so as to match most forehead curvatures. The object of the three pronged rubber bumper (not shown) is to prevent sideward turning of the face during measurement that could contribute to measurement errors in horizontal decentration. The optician 45 then performs the vertical and horizontal decentration measurements described above.

Specific embodiments of an apparatus for measuring pupillary height according to the present invention have been described for the purpose of illustrating the manner in which the invention may be made and used. It should be understood that implementation of other variations and modifications of the invention and its various aspects will be apparent to those skilled in the art, and that the invention is not limited by the specific embodiments described. It is therefore contemplated to cover by the present invention any and all modifications, variations, or equivalents that fall within the true spirit and scope of the basic underlying principles disclosed and claimed herein.

What is claimed is:

1. An apparatus for measuring in combination, vertical and horizontal decentration of a pupil of a patient relative to a spectacle frame, the apparatus comprising:

a housing having a distal end defining at least one target aperture, said housing having a proximal end opposite the distal end;

an eye-piece disposed toward the proximal end, said eye-piece permitting an operator to observe the pupil of the patient through the target aperture such that the eye-piece, the target aperture, the spectacle frame, and the pupil of the patient are in operative alignment;

at least two adjustable horizontal reference markers, each operatively coupled to the housing and vertically displaceable relative thereto, one of the horizontal reference markers configured to be aligned with and intersect a center of the pupil, and the other horizontal reference marker configured to be aligned with at least one of an upper edge and a lower edge of the spectacle frame;

said at least two horizontal reference markers operatively coupled to a circuit which provides an electrical signal corresponding to a measurement of a vertical distance between the center of the pupil and at least one of the upper and lower edges of the spectacle frame, said vertical distance representing the vertical decentration;

at least two adjustable vertical reference markers, each operatively coupled to the housing and horizontally displaceable relative thereto, one of the vertical reference markers configured to be aligned with and intersect the center of the pupil, and the other vertical reference marker configured to be aligned with at least one of a temporal edge and a nasal edge of the spectacle frame; and said at least two vertical reference markers operatively coupled to a circuit which provides an electrical signal corresponding to a measurement of a horizontal distance between the center of the pupil and at least one of the temporal and nasal edges of the spectacle frame, said horizontal distance representing the horizontal decentration.

2. An apparatus for measuring in combination, vertical and horizontal decentration of a pupil of a patient relative to a spectacle frame, the apparatus comprising:

a housing having a distal end defining at least one target aperture, said housing having a proximal end opposite the distal end;

an eye-piece disposed toward the proximal end, said eye-piece permitting an operator to observe the pupil of the patient through the target aperture such that the eye-piece, the target aperture, the spectacle frame, and the pupil of the patient are in operative alignment;

an adjustable upper, lower, and center horizontal reference marker, each operatively coupled to the housing and vertically displaceable relative thereto, said upper and lower horizontal reference markers configured to determine the position of an upper edge and lower edge of the spectacle frame, respectively, said center horizontal reference marker configured to be aligned with and intersect a center of the pupil;

said upper, lower, and center horizontal reference markers operatively coupled to a circuit which provides an electrical signal corresponding to a measurement of a vertical distance between the center horizontal reference marker and the upper and lower reference markers, respectively, said vertical distance representing the vertical decentration;

an adjustable left, right, and center vertical reference marker, each operatively coupled to the housing and horizontally displaceable relative thereto, said left and right vertical reference markers configured to determine the position of a temporal edge and a nasal edge of the spectacle frame, respectively, said center vertical reference marker configured to be aligned with and intersect the center of the pupil; and said left, right, and center vertical reference markers operatively coupled to a circuit which provides an electrical signal corresponding to a measurement of a horizontal distance between the center vertical reference marker and the left and right reference markers, respectively, said horizontal distance representing the horizontal decentration.

3. An apparatus for measuring in combination, vertical and horizontal decentration of a pupil of a patient relative to a spectacle frame, the apparatus comprising:

a housing having a distal end defining at least one target aperture, said housing having a proximal end opposite the distal end;

an eye-piece disposed toward the proximal end, said eye-piece permitting an operator to observe the pupil of the patient through the target aperture such that the eye-piece, the target aperture, the spectacle frame, and the pupil of the patient are in operative alignment;

a horizontal reference marker configured to be aligned with and intersect a center of the pupil;

at least one horizontal platform configured to contact one of an upper and lower edge of the spectacle frame;

said horizontal reference marker and said at least one horizontal platform operatively coupled to the housing and vertically displaceable relative thereto;

said horizontal reference marker and said at least one horizontal platform operatively coupled to a circuit which provides an electrical signal corresponding to a measurement of a vertical distance between the horizontal reference marker and the at least one horizontal platform, said vertical distance representing the vertical decentration;

at least two adjustable vertical reference markers, each operatively coupled to the housing and horizontally displaceable relative thereto, one of the vertical reference markers configured to be aligned with and intersect the center of the pupil and the other configured to be aligned with at least one of a temporal edge and a nasal edge of the spectacle frame; and said at least two vertical reference markers operatively coupled to a circuit which provides an electrical signal corresponding to a measurement of a horizontal distance between the center of the pupil and at least one of the temporal and nasal edges of the spectacle frame, said horizontal distance representing the horizontal decentration.

4. The apparatus according to claim 3 wherein the vertical reference markers are adjacent the target apertures and are displaceable in a direction relative to the target apertures so as to be maintained in a spaced-apart parallel orientation relative to the target apertures such that parallax measurement error is substantially eliminated.

5. The apparatus according to claim 3 further including an upper and a lower adjustable horizontal platform, said upper and lower platforms arranged to contact an upper and a lower edge of the spectacle frame, respectively, said horizontal reference marker configured to be aligned with and intersect the center of the pupil to provide an indication of a vertical distance between the horizontal reference marker and the upper and lower platforms, respectively.

6. The apparatus according to claim 3 wherein the vertical reference markers include a left, right, and center vertical reference markers, said left and right vertical reference markers arranged to be aligned with the left and the right edges of the spectacle frame, respectively, the center vertical reference marker configured to be aligned with and intersect the center of the pupil while disposed vertically between the left and right vertical reference markers.

7. The apparatus according to claim 3 further including means for establishing and maintaining the housing at a fixed position relative to the spectacle frame, said means for establishing and maintaining being oriented relative to a longitudinal axis of the housing, the longitudinal axis passing between the target apertures.

8. The apparatus according to claim 7 further including a chin rest and a forehead rest disposed along the longitudinal axis and external to the housing, the chin rest vertically displaceable relative the housing, and the forehead rest forwardly and backwardly displaceable along the longitudinal axis.

9. The apparatus according to claim 3 wherein the circuits which provide electrical signals corresponding to the measurement of a horizontal distance and a vertical distance include electronic means configured to receive the electronic signals and visually indicate numerical values corresponding to the electronic signals.

10. An apparatus for measuring in combination, vertical and horizontal decentration of a pupil of a patient relative to a spectacle frame, the apparatus comprising:

a housing having a distal end defining at least one target aperture, said housing having a proximal end opposite the distal end;

an eye-piece disposed toward the proximal end, said eye-piece permitting an operator to observe the pupil of the patient through the target aperture such that the eye-piece, the target aperture, the spectacle frame, and the pupil of the patient are in operative alignment;

a horizontal reference marker configured to be aligned with and intersect a center of the pupil;

an upper and a lower horizontal platform configured to contact an upper and lower edge of the spectacle frame, respectively;

said horizontal reference marker and the horizontal platforms operatively coupled to the housing and vertically displaceable relative thereto;

said horizontal reference marker and said horizontal platforms operatively coupled to a circuit which provides an electrical signal corresponding to a measurement of a vertical distance between the horizontal reference marker and the upper and lower platforms, respectively, said vertical distance representing the vertical decentration;

at least two adjustable vertical reference markers, each operatively coupled to the housing and horizontally displaceable relative thereto, one of the vertical reference markers configured to be aligned with and intersect the center of the pupil, and the other vertical reference marker configured to be aligned with at least one of a temporal edge and a nasal edge of the spectacle frame; and said at least two vertical reference markers operatively coupled to a circuit which provides an electrical signal corresponding to a measurement of a horizontal distance between the center of the pupil and at least one of the temporal and nasal edges of the spectacle frame, said horizontal distance representing the horizontal decentration.

11. An apparatus for measuring in combination, vertical and horizontal decentration of a pupil of a patient relative to a spectacle frame, the apparatus comprising:

a housing having a distal end defining at least one target aperture, said housing having a proximal end opposite the distal end;

an eye-piece disposed toward the proximal end, said eye-piece permitting an operator to observe the pupil of the patient through the target aperture such that the eye-piece, the target aperture, the spectacle frame, and the pupil of the patient are in operative alignment;

a horizontal reference marker configured to be aligned with and intersect a center of the pupil;

at least one horizontal platform configured to contact one of an upper and lower edge of the spectacle frame;

said horizontal reference marker and said at least one horizontal platform operatively coupled to the housing and vertically displaceable relative thereto;

said horizontal reference marker and said at least one horizontal platform operatively coupled to a circuit which provides an electrical signal corresponding to a measurement of a vertical distance between the horizontal reference marker and the at least one horizontal platform, said vertical distance representing the vertical decentration;

an adjustable left, right, and center vertical reference marker, each operatively coupled to the housing and horizontally displaceable relative thereto, said left and right vertical reference markers configured to determine the position of a temporal edge and a nasal edge of the spectacle frame, respectively, said center vertical reference marker configured to be aligned with and intersect the center of the pupil; and said left, right, and center vertical reference markers operatively coupled to a circuit which provides an electrical signal corresponding to a measurement of a horizontal distance between the center vertical reference marker and the left and right reference markers, respectively, said horizontal distance representing the horizontal decentration.

12. An apparatus for measuring horizontal decentration of a pupil of a patient relative to a spectacle frame, the apparatus comprising:

a housing having a distal end defining at least one target aperture, said housing having a proximal end opposite the distal end;

an eye-piece disposed toward the proximal end, said eye-piece permitting an operator to observe the pupil of the patient through the target aperture such that the eye-piece, the target aperture, the spectacle frame, and the pupil of the patient are in operative alignment;

at least two adjustable vertical reference markers, each operatively coupled to the housing and horizontally displaceable relative thereto, one of the vertical reference markers configured to be aligned with and intersect the center of the pupil, and the other vertical reference marker configured to be aligned with at least one of a temporal edge and a nasal edge of the spectacle frame; and said at least two vertical reference markers operatively coupled to a circuit which provides an electrical signal corresponding to a measurement of a horizontal distance between the center of the pupil and at least one of the temporal and nasal edges of the spectacle frame, said horizontal distance representing the horizontal decentration.

13. A method for measuring in combination, vertical and horizontal decentration of a pupil of a patient relative to a spectacle frame, the method comprising the steps of:

a) operatively fixing a position of a housing relative to a head of a patient, said housing having a proximal and a distal end, said distal end defining at least one target aperture so that a line of sight of the patient is directed into the at least one target aperture;

b) observing the pupil of the patient by viewing the pupil through an eye-piece disposed toward the proximal end of the housing such that the eye-piece, the target aperture, the spectacle frame, and said pupil of the patient are in operative alignment;

c) aligning a lower horizontal platform and an upper horizontal platform with lower and upper edges of the spectacle frame, respectively;

d) aligning a horizontal reference marker with a center of the pupil so that the horizontal reference marker intersects said center of the pupil;

e) determining a measurement of the vertical decentration represented by a position of the horizontal reference marker relative to the position of the upper and lower horizontal platforms, respectively;

f) aligning a left and a right vertical reference marker with a left and a right edge of a single lens portion of the spectacle frame, respectively;

g) aligning a center vertical reference marker with the center of the pupil so that the vertical reference marker intersects said center of the pupil;

h) determining a measurement of the horizontal decentration represented by a position of the center vertical reference marker relative to the position of the left and right vertical reference markers, respectively;

i) repeating steps b) through h) for the other pupil of the patient; and j) displaying the values of the measured vertical and horizontal decentration.

14. A method for measuring in combination vertical and horizontal decentration with respect to pupil of a patient and a spectacle frame, the method comprising the steps of:

a) operatively fixing a position of a measuring device relative to a head of a patient, said measuring device having a proximal and a distal end, said distal end defining at least one target aperture so that a line of sight of the patient is directed into the at least one target aperture;

b) determining a vertical height of the spectacle frame measured between an upper and lower edge of the spectacle frame;

c) determining a vertical center of the pupil of the patent relative to the vertical height of the spectacle frame;

d) dividing the vertical height of the spectacle frame by two and subtracting the value of the vertical center of the pupil to obtain a value representing the vertical decentration;

e) determining a horizontal width of a single lens portion of the spectacle frame measured between a left and a right edge of the single lens portion of the frame spectacle;

f) determining a horizontal center of the pupil of the patient relative to the horizontal width;

g) dividing the horizontal width by two and subtracting the value of the horizontal center of the pupil to obtain a value representing horizontal decentration;

h) repeating steps b) through f) for the other pupil of the patient; and j) displaying the values of the measured vertical and horizontal decentration.

* * * * *